US009868558B2

(12) United States Patent
Holmes

(10) Patent No.: US 9,868,558 B2
(45) Date of Patent: Jan. 16, 2018

(54) PHARMACEUTICAL STORAGE AND RETRIEVAL SYSTEM AND METHODS OF STORING AND RETRIEVING PHARMACEUTICALS

(75) Inventor: William K. Holmes, San Diego, CA (US)

(73) Assignee: RXSAFE, LLC, San Marcos, CA (US)

( * ) Notice: Subject to any disclaimer, the term of this patent is extended or adjusted under 35 U.S.C. 154(b) by 578 days.

(21) Appl. No.: 12/808,748

(22) PCT Filed: Dec. 19, 2008

(86) PCT No.: PCT/US2008/087858
§ 371 (c)(1),
(2), (4) Date: Apr. 8, 2011

(87) PCT Pub. No.: WO2009/086217
PCT Pub. Date: Jul. 9, 2009

(65) Prior Publication Data
US 2011/0184751 A1    Jul. 28, 2011

Related U.S. Application Data

(60) Provisional application No. 61/015,119, filed on Dec. 19, 2007, provisional application No. 61/091,261, filed on Aug. 22, 2008.

(51) Int. Cl.
*G06Q 50/00* (2012.01)
*B65B 57/00* (2006.01)
(Continued)

(52) U.S. Cl.
CPC .............. *B65B 57/00* (2013.01); *B65G 1/06* (2013.01); *G06F 19/3462* (2013.01);
(Continued)

(58) Field of Classification Search
USPC .......................................................... 705/2
See application file for complete search history.

(56) References Cited

U.S. PATENT DOCUMENTS

| 4,019,793 A | 4/1977 | Gerding |
| 4,267,942 A | 5/1981 | Wick, Jr. et al. |

(Continued)

FOREIGN PATENT DOCUMENTS

| WO | 2009086217 | 7/2009 |
| WO | 2012027741 | 3/2012 |

OTHER PUBLICATIONS

Google patents search, Jan. 6, 2016.
PCT/US2008/087858 International Search Report and Written Opinion dated Oct. 8, 2009 (5 pages).

*Primary Examiner* — Sean K Hunter
*Assistant Examiner* — Gregory Lultschik
(74) *Attorney, Agent, or Firm* — Michael Best & Friedrich LLP

(57) ABSTRACT

A pharmaceutical storage and retrieval device and a method of accessing and loading the device. The device includes a housing, at least one port with controlled access to inventory stored within the device, a robotic transfer mechanism for moving inventory items to and from the controlled port, software for tracking the inventory and users of the device, and an interface with the pharmacy software system to track and monitor which inventory is authorized for access by each user and which inventory is needed to fill a prescription.

17 Claims, 31 Drawing Sheets

(51) Int. Cl.
*G06Q 50/22* (2012.01)
*G07F 9/02* (2006.01)
*G07F 11/16* (2006.01)
*G07F 11/44* (2006.01)
*G07F 17/00* (2006.01)
*B65G 1/06* (2006.01)
*G06F 19/00* (2011.01)

(52) U.S. Cl.
CPC ............ *G06Q 50/22* (2013.01); *G07F 9/026* (2013.01); *G07F 11/165* (2013.01); *G07F 11/44* (2013.01); *G07F 17/0092* (2013.01); *G06F 19/327* (2013.01)

(56) References Cited

U.S. PATENT DOCUMENTS

| | | | |
|---|---|---|---|
| 4,546,901 A | 10/1985 | Buttarazzi | |
| 4,635,053 A | 1/1987 | Banks et al. | |
| 4,695,954 A | 9/1987 | Rose et al. | |
| 5,047,948 A | 9/1991 | Turner | |
| 5,208,762 A | 5/1993 | Charhut et al. | |
| 5,337,919 A | 8/1994 | Spaulding et al. | |
| 5,468,110 A | 11/1995 | McDonald et al. | |
| 5,593,267 A | 1/1997 | McDonald et al. | |
| 5,597,995 A | 1/1997 | Williams et al. | |
| 5,671,592 A | 9/1997 | Yuyama et al. | |
| 5,797,515 A | 8/1998 | Liff et al. | |
| 5,883,370 A | 3/1999 | Walker et al. | |
| 5,883,806 A | 3/1999 | Meador et al. | |
| 5,893,697 A | 4/1999 | Zini et al. | |
| 5,905,653 A | 5/1999 | Higham et al. | |
| 5,907,493 A | 5/1999 | Boyer et al. | |
| 5,950,832 A | 9/1999 | Perlman | |
| 6,006,946 A | 12/1999 | Williams et al. | |
| 6,036,812 A | 3/2000 | Williams et al. | |
| 6,175,779 B1 | 1/2001 | Barrett | |
| 6,256,967 B1 | 7/2001 | Hebron et al. | |
| 6,364,517 B1 | 4/2002 | Yuyama et al. | |
| 6,370,841 B1 | 4/2002 | Chudy et al. | |
| 6,449,927 B2 | 9/2002 | Hebron et al. | |
| 6,604,019 B2 | 8/2003 | Ahlin et al. | |
| 6,609,047 B1 | 8/2003 | Lipps | |
| 6,650,964 B2 | 11/2003 | Spano, Jr. et al. | |
| 6,883,681 B1 | 4/2005 | Coughlin et al. | |
| 6,892,941 B2 | 5/2005 | Rosenblum | |
| 6,963,791 B1 | 11/2005 | Frederick et al. | |
| 7,006,893 B2 | 2/2006 | Hart et al. | |
| 7,123,989 B2 | 10/2006 | Pinney et al. | |
| 7,151,982 B2 | 12/2006 | Liff et al. | |
| 7,182,105 B1 | 2/2007 | Feehan et al. | |
| 7,210,598 B2 | 5/2007 | Gerold et | |
| 7,228,198 B2 | 6/2007 | Vollm et al. | |
| 7,263,410 B1 | 8/2007 | Frederick et al. | |
| 7,263,411 B2 | 8/2007 | Shows et al. | |
| 7,289,879 B2 | 10/2007 | William et al. | |
| 7,316,536 B2 | 1/2008 | Evans et al. | |
| 7,527,139 B2 * | 5/2009 | Hasenfratz et al. | 198/347.2 |
| 7,630,788 B1 * | 12/2009 | Reese | 700/216 |
| 7,783,383 B2 * | 8/2010 | Eliuk et al. | 700/245 |
| 8,121,725 B2 | 2/2012 | Baker et al. | |
| 8,342,400 B1 * | 1/2013 | Reese | 235/385 |
| 2004/0004415 A1 | 1/2004 | Melching | |
| 2004/0054607 A1 * | 3/2004 | Waddington | G06Q 10/087 705/28 |
| 2004/0113786 A1 * | 6/2004 | Maloney | G07C 9/00103 340/568.1 |
| 2004/0133483 A1 | 7/2004 | Potter et al. | |
| 2004/0176873 A1 | 9/2004 | Kim | |
| 2005/0113968 A1 | 5/2005 | Williams et al. | |
| 2005/0234591 A1 | 10/2005 | Kim | |
| 2005/0236417 A1 | 10/2005 | Baker et al. | |
| 2005/0263537 A1 | 12/2005 | Gerold et al. | |
| 2006/0041330 A1 | 2/2006 | Ansari et al. | |
| 2006/0058918 A1 | 3/2006 | Handfield et al. | |
| 2006/0224459 A1 * | 10/2006 | Aramaki | G01G 19/414 705/22 |
| 2006/0259195 A1 | 11/2006 | Eliuk et al. | |
| 2006/0277110 A1 * | 12/2006 | Witter | G06F 19/327 705/26.1 |
| 2007/0043469 A1 * | 2/2007 | Draper | 700/231 |
| 2007/0191983 A1 * | 8/2007 | Griffits | A47G 19/2227 700/213 |
| 2007/0208589 A1 | 9/2007 | Kugler et al. | |
| 2007/0208598 A1 | 9/2007 | McGrady et al. | |
| 2008/0029601 A1 | 2/2008 | Clarke et al. | |
| 2008/0178605 A1 | 7/2008 | Wesley et al. | |
| 2008/0264967 A1 * | 10/2008 | Schifman | G07F 11/44 221/133 |
| 2010/0030667 A1 | 2/2010 | Chudy et al. | |
| 2010/0125461 A1 | 5/2010 | Heald | |
| 2010/0198401 A1 | 8/2010 | Waugh et al. | |
| 2010/0316979 A1 | 12/2010 | Von Bismarck | |
| 2011/0288883 A1 | 11/2011 | Knoth | |
| 2012/0081225 A1 | 4/2012 | Waugh et al. | |

* cited by examiner

PHARMACEUTICAL STORAGE AND RETRIEVAL SYSTEM AND METHODS OF STORING AND RETRIEVING PHARMACEUTICALS

RELATED APPLICATIONS

This application is a non-provisional application of and claims priority to U.S. Provisional Patent Application Ser. No. 61/091,261, filed on Aug. 22, 2008, and U.S. Provisional Patent Application Ser. No. 61/015,119, filed on Dec. 19, 2007. The contents of both applications are incorporated herein by reference.

BACKGROUND OF THE INVENTION

Many modern pharmacies continue to store their bulk pharmaceutical inventory on open shelves. These shelves are usually stocked and accessible by multiple technicians, clerks, and pharmacists. Such shelving arrangements are an inefficient use of space and make accurate monitoring of inventory challenging. Additionally, tracking how fast a particular prescription medication gets used and when that medication needs restocking takes deliberate attention. Further, even with surveillance cameras, there are times when the inventory is not satisfactorily monitored, and both authorized and unauthorized persons may have access to and misappropriate the inventory.

A typical pharmacy workflow generally includes three processes: (1) a front end process; (2) a filling process; and (3) a storage, selling, verification of prescription accuracy, and consulting with customer process. The front end process generally includes a clearinghouse aspect and drug utilization review where an intake worker receives insurance information, verifies that the prescription is valid, and inputs the necessary information into the pharmacy management system. The filling process includes filling a prescription by a pharmacy technician or pharmacist who obtains a bottle of medication from the shelf, pours the medication on a counting pad, counts the appropriate number of pills, pours the pills into a bottle, labels the bottle, prints the supporting consumer medication information, bags the bottle and literature, and places the bag in a dispensing area. The third process includes a pharmacist verifying that the correct medication is in the customer vial when compared to the prescription, collecting money from the customer for the prescription, and consulting with the customer regarding usage and side effects of the medication. If a pharmacist has not already discussed the medication with the customer, a pharmacist must do so during this third process in accordance with the State Board of Pharmacy regulations.

SUMMARY OF THE INVENTION

The present invention relates to a storage and retrieval system and method, and more particularly to a pharmaceutical storage and retrieval device and associated methods. The pharmaceutical storage and retrieval device modifies the typical pharmacy workflow for filling a prescription (the second process discussed above) and brings the work to the worker. The machine provides about 4,500 plus bottles of medication to be within reach of the worker to improve consistency, efficiency, and cost reductions to the pharmacy.

In one embodiment, the present invention provides a pharmaceutical storage and retrieval system having a housing, at least one port with controlled access to inventory stored within the device, a robotic transfer mechanism for moving inventory items to and from the controlled port, software for tracking of inventory and users of the machine, and an interface with the pharmacy software system to track and monitor which inventory is authorized for access by each user and which inventory is needed, and inventory accessed by each user.

In another embodiment, the invention provides methods for storing, retrieving, and monitoring pharmaceutical inventory. In some embodiments, the method can be used in a pharmacy for storing, retrieving, monitoring, and limiting access to prescription medications.

In one particular embodiment, the invention provides a method of filling a prescription. The method comprises verifying identification information of a user, obtaining prescription information, the prescription information including a medication type, determining a shelf location of a container having the medication type, retrieving the container from the identified shelf location, positioning the container on an access port, weighing the container to determine a weight value of the container, reading a label on the container, opening a door to the port if the weight value of the container matches a predetermined weight value of the container, and removing the container from the port to fill the prescription.

In another particular embodiment, the invention provides a method of stocking a pharmaceutical storage and retrieval device. The method comprises verifying identification information of a user of the system, opening a door to a port of the device if the user is verified, positioning the inventory item in the port, weighing the inventory item to determine a weight value of the inventory item, storing the weight value of the inventory item in the device, reading a label on the inventory item to identify a medication type, storing the medication type in the device, identifying an available space in the device for the inventory item, moving the inventory item from the port to the identified space, and linking the inventory item and the identified space and storing the linked information in the device.

In another embodiment, the invention provides a software program stored in a computer readable medium accessible by a computer processor. The software program comprises a stock module operable to transmit instructions to a pharmacy storage and retrieval device to identify a size of a container and position the container within the pharmacy storage and retrieval device, and an optimization module in communication with the stock module, the optimization module operable to identify an optimal location within the pharmacy storage and retrieval device to position the container based on the size of the container.

Other aspects of the invention will become apparent by consideration of the detailed description and accompanying drawings.

DETAILED DESCRIPTION

Figure 1:
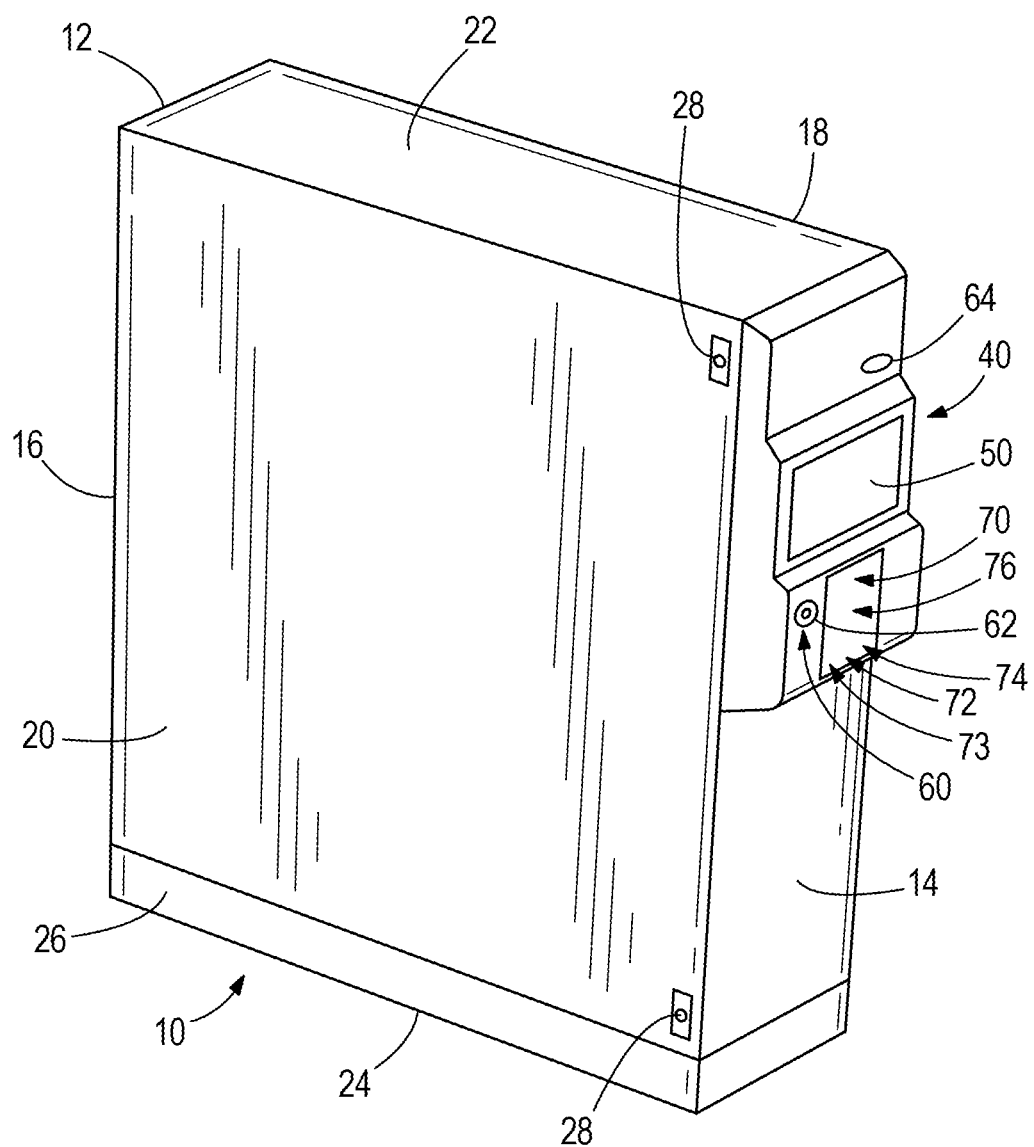
FIG. 1 is a front perspective view of a pharmaceutical storage and retrieval device according to some embodiments of the present invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a pharmaceutical storage and retrieval device 10 according to an embodiment of the present invention. The pharmaceutical storage and retrieval device 10 includes a housing 12 having a front 14 and a rear 16, a right side 18 and a left side 20, and a top 22 and a bottom 24. The housing 12 can also include a base 26 adjacent to the bottom 24 of the device 10, as illustrated. In some embodiments, wheels (not shown) are coupled to the base 26 for ease of movement of the device 10. In some embodiments, the side panels 18, 20 of the housing 12 can be opened by unlocking one or more locks 28 with a key. In the illustrated embodiment, the locks 28 are located at the top 22 and bottom 24 near the front of the right 18 and left 20 sides, but in alternate embodiments, the one or more locks 28 can be located elsewhere on the housing 12. In alternate embodiments, the housing 12 can embody other suitable shapes such as, for example, cylindrical or tubular, another polygonal shape, or the like. In some embodiments, the dimensions of the housing are about sixteen inches from side 18 to side 20, about sixty inches from front 14 to rear 16, and about seventy-eight inches from top 22 to bottom 24. In other embodiments, the dimensions of the housing are about twenty inches from side 18 to side 20, about eighty-four inches from front 14 to rear 16, and about ninety inches from top 22 to bottom 24. However in alternate embodiments, the housing 12 can have many different suitable dimensions.

The pharmaceutical storage and retrieval device 10 can include an interface panel 40, as illustrated in FIG. 1. In the illustrated embodiment, the interface panel 40 is located on the front 14 of the device 10 and may be integrally formed with the housing 12. However, in additional embodiments, the interface panel 40 can be located elsewhere on the device, such as, for example, to the right side 18, to the left side 20, or the like. The interface panel 40 includes a user display screen 50 for input and output of information to and from a user. In some embodiments, the user display screen 50 can be a touch screen, a graphical user interface, or the like. An access control device 60 can also be incorporated onto the interface panel 40. In some embodiments, the access control device 60 can include a biometric sensing device 62. The biometric sensing device 62 can detect biometric characteristics of a user such as fingerprint, iris, voice, etc., or combinations thereof. In some embodiments, the access control device 60 can include other access limiting mechanisms in addition to or in place of the biometric sensing device 62, such as, for example, identification card swiping, access code input, or the like. Access to the device 10 can additionally be monitored by a video camera 64 mounted on or within the housing 12.

Alternatively, the display screen 50 can be located remotely from the device 10. For example, a pharmacy employing one or more of the devices 10 can embed or incorporate the display screen 50 and/or its functions, for example, on a separate computer. In other embodiments, the access control device 60 can be stationed remote from the device 10. For example, a pharmacy employing one or more of the devices 10 can include the access control device 60, for example, on a separate computer stationed adjacent to or near the device 10.

The device 10 also can include a first port 70 for receiving a medication being input to the device 10. The port 70 can include a weight measuring device, such as a scale 72 therein for weighing the inventory item(s) that are input to the device 10. In some embodiments, the scale 72 can be rotated so as to turn the inventory item being weighed to a desired orientation. The first port 70 also can include a platform 73 located near to or covering the scale 72. In some embodiments, the platform 73 can be rotated so as to turn the inventory to a desired orientation or to move or transport the inventory item to a different location within the housing 12, such as, for example, onto the scale 72. A scanner 74 is located adjacent to the port 70. In some embodiments, the scanner 74 is a barcode scanner. In other embodiments, the scanner 74 can be another type of detector, such as, for example, a profile contrast detector, a camera, another type of visual imaging detector, or the like. The port 70 includes a door 76 movably controlled by the device 10 to block or allow access to the port 70. In other embodiments, the port 70 can have no door 76 or a different mechanism to selectively block and allow access to the port 70.

The device 10 can include a second port for receiving and holding an inventory item such as a medication being requested from the device 10. The port can include a door movably controlled by the device 10 to block or allow access to the port. In addition, the device 10 can include additional interface panels 40.

The device 10 can include a loading port having a loading scale, and a loading scanner. The loading port can also include a grabbing device to facilitate loading of inventory into the machine 10, such that bulk pharmaceuticals can be loaded onto the angled ramp all at once and the machine 10 will then automatically take in the bulk pharmaceuticals one container at a time. Alternatively, the interface panel 40 can include multiple access ports, discussed below. For example, the inventory machine 10 can include a plurality of ports. One of the ports can be an input port, whereas another one of the ports can be an output port. In such constructions, both the input and output ports can include respective scales for weighing items to be dispensed and/or stocked. Additionally, a robotic arm can also be used to rotate the objects of interest that are positioned on the scales for scanning purposes.

Figure 2:
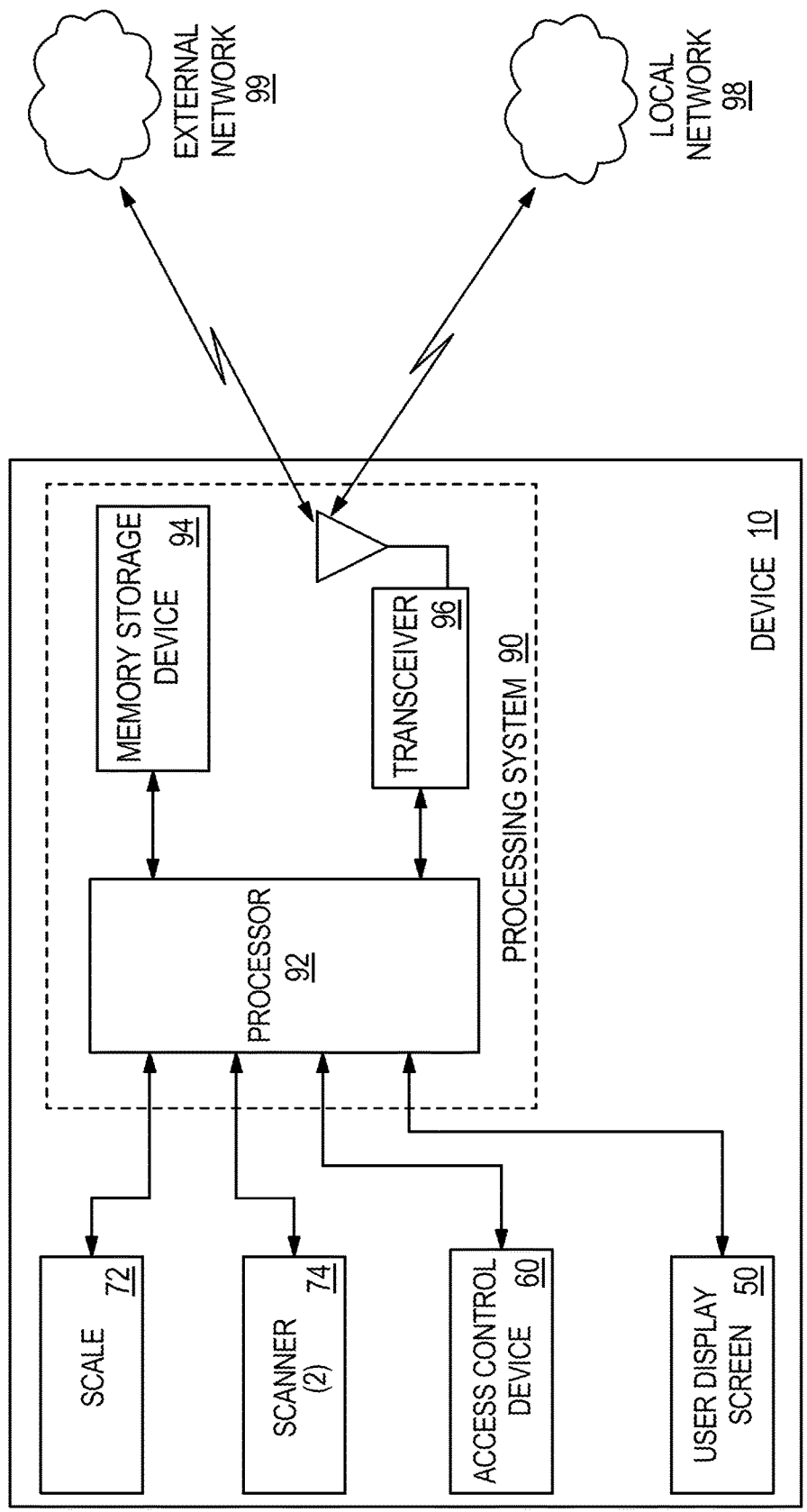
FIG. 2 is a schematic diagram of the pharmaceutical storage and retrieval device of FIG. 1.

As illustrated in FIG. 2, the pharmaceutical storage and retrieval device 10 can include a processing system 90. The processing system 90 includes a CPU or a microprocessor 92, a memory storage device 94, and a transceiver 96. The microprocessor 92 is connected to and/or in communication with the scale 72, the scanner 74, the access control device 60, the user display screen 50, and the memory storage device 94 to monitor and store information regarding the inventory in the device 10 and profiles of the users of the device 10. The microprocessor 92 is also connected to and/or in communication with the transceiver 96. The transceiver 96 communicates information regarding the inventory and the users between the device 10 and a pharmacy management system (PMS) and software over one or more local networks 98. In additional embodiments, the local network 98 can include other types of systems and software. In some embodiments, the processing system 90 can also communicate with external networks 99, such as the manufacturers or distributors of the inventory that is stored in the device 10. In other embodiments, the user display screen 50 and its functions are included in a separate computer that is part of the PMS network. In such cases, components such as the scale 72, the scanner 74, and the access control device 60 can be stationed at the pharmaceutical storage and retrieval device 10. Other components such as the user display screen 50 can be stationed in a separate computer.

Figure 3:
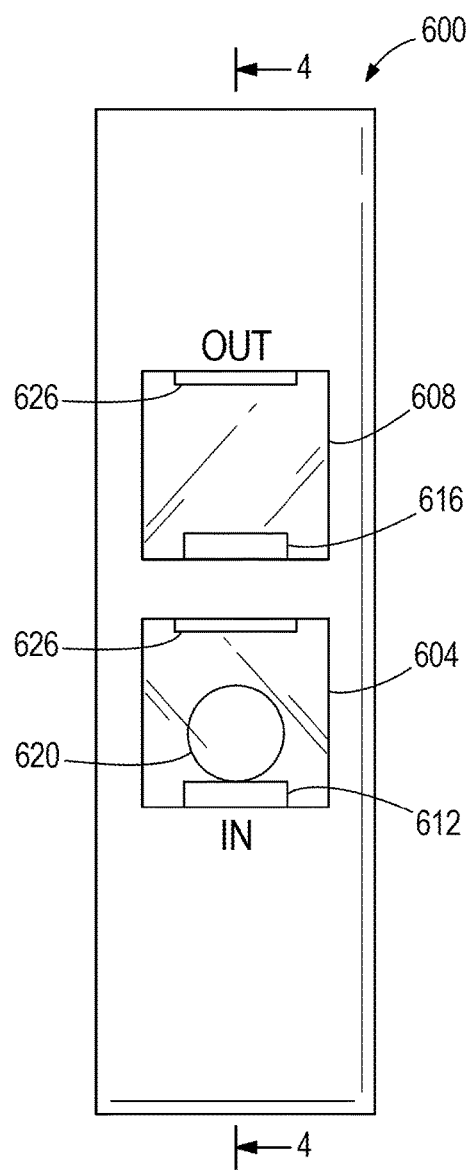
FIG. 3 a front view of a pharmaceutical storage and retrieval device according to the present invention.
Figure 4:
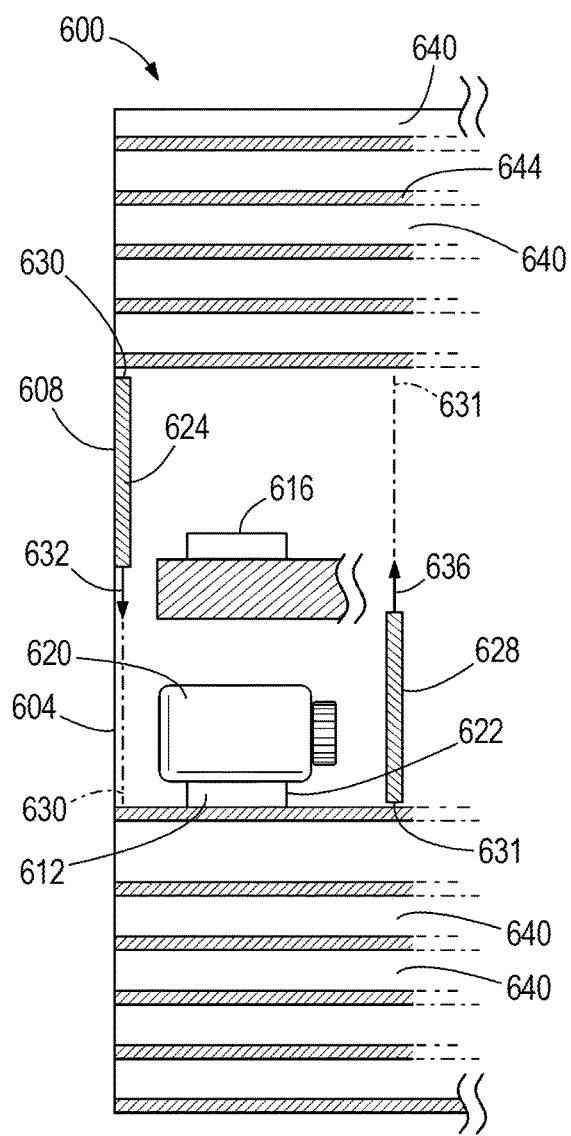
FIG. 4 is a sectional view of the pharmaceutical storage and retrieval device of FIG. 3 taken along the line 4-4 of FIG. 3.

FIG. 3 shows a front view of an alternate pharmaceutical storage and retrieval device 600, and FIG. 4 shows a sectional view of the device 600 of FIG. 3 taken along line 4-4 of FIG. 3. The device 600 includes, among other things as shown in FIG. 1, an input port 604 for stocking purposes and an output port 608 for dispensing purposes, and their respective platforms 612, 616. An exemplary bottle 620 is placed on the platform 612 of the input port 604. The bottle 620 can be oriented in any direction on the platform 612, 616 for suitable operation of the device 600. The port 604 can include a scale 622 operable to weigh the bottle 620. The port 604 also can include a scanner 626 operable to acquire an image of the bottle 620. It should be understood that the input and output ports 604 and 608 can also be placed in any other suitable positions. For example, the output port 608 can be positioned below the input port 604. For another example, the output port 608 can also be positioned next to the input port 604.

As best seen in FIG. 4, the device 600 also includes front and back doors 624, 628 positioned at respective front and back planes 630, 631, and configured to retrievably move in directions indicated by arrows 632 and 636, respectively. The front door 624 controls access to one of the input port 604 and the output port 608. Particularly, the front door 624 is controlled such that only one of the input port 604 and the output port 608 is accessible from the outside of the device 600. For example, as shown, when the front door 624 is at the front plane 630 and aligns with the output port 608, only the input port 604 is accessible from the outside of the device 600.

Conversely, the back door 628 can control access to the interior of the device 600. In the embodiment shown, the back door 628 is controlled such that only one of the platforms 612, 616 is accessible by the robotic arm 144 (discussed below) from the interior of the device 600. For example, as shown, when the back door 628 is at the back plane 631 and aligns with the input port 604, the back door 628 prevents any access by the robotic arm 144 into the input port 604.

Furthermore, in some embodiments, the front and back doors 624, 628 are configured to move in opposite directions simultaneously. For example, as shown, when the front door 624 closes the output port 608 at the front plane 630, the input port 604 is open. Meanwhile, the back door 628 is aligned with the input port 604 at the back plane 631. In this way, only the input port 604 is accessible from the outside, and the back door 628 prevents any access from the outside of the device 600 into the interior of the device 600 through the input port 604. Conversely, when the front door 624 closes the input port 604 at the front plane 630, the output port 608 is open. Meanwhile, the back door 628 is aligned with the output port 608 at the back plane 631. In this way, only the output port 608 is accessible from the outside, and the back door 628 prevents any access from the outside of the device 600 into the interior of the device 600 through the output port 608.

Figure 5:
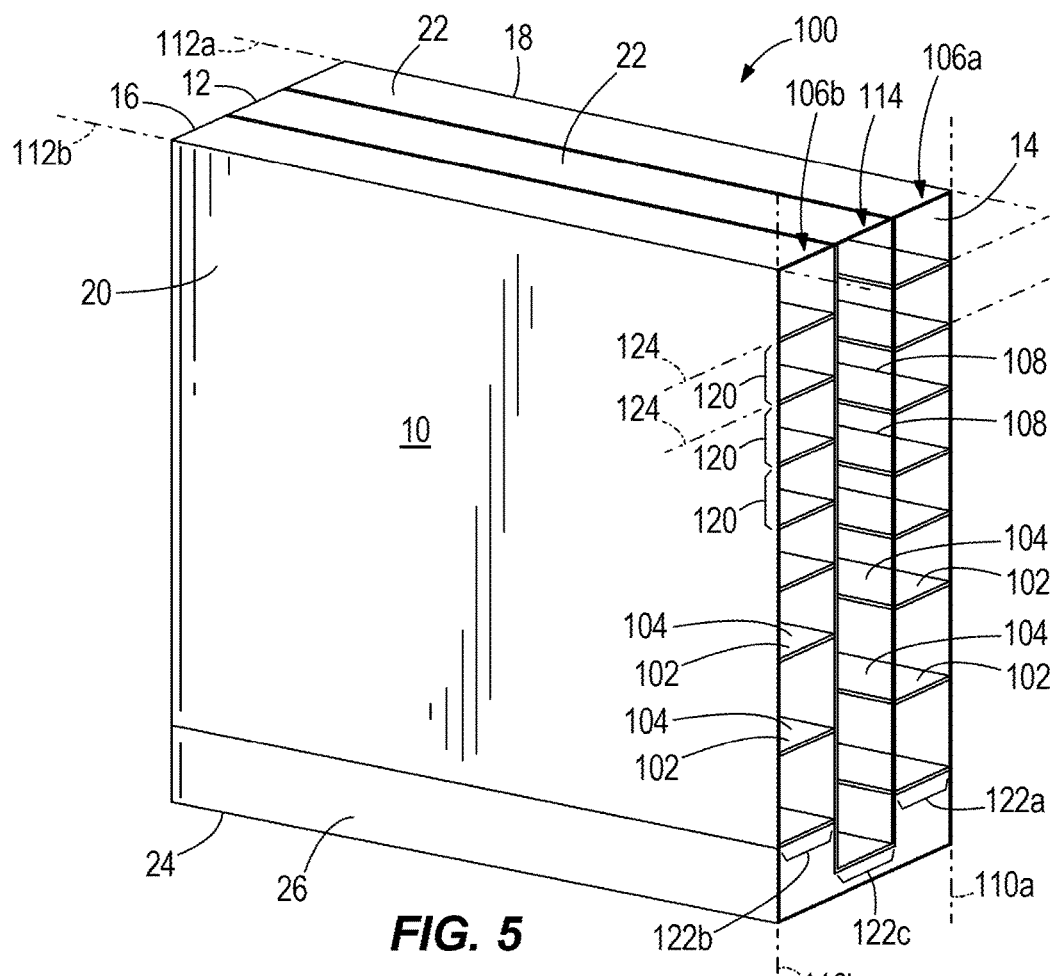
FIG. 5 is a front perspective view of a shelving system within the pharmaceutical storage and retrieval device.

FIG. 5 illustrates an interior view of the pharmaceutical storage and retrieval device 10, 600 according to one embodiment of the present invention. The device 10, 600 includes a shelving system 100 having a plurality of shelves 102 within the housing 12. Each shelf 102 has a generally planar surface 104, and the planar surfaces 104 of the shelves 102 are substantially parallel to each other. The planar surfaces 104 are also generally aligned with two horizontal axes 112 and 124, which are substantially perpendicular to each other, one horizontal axis 112 extending from front 14 to the rear 16 of the device 10, 600 and the other horizontal axis 124 extending from the right side 18 to the left side 20 of the device 10, 600.

The shelves 102 can be arranged into columns of shelves 106, wherein an edge 108 of each shelf 102 is substantially aligned along a vertical axis 110. The vertical axis 110 extends from the bottom 24 of the device 10 to the top 22 of the device 10, 600 and the shelves 102 are stacked generally from the bottom 24 to the top 22 of the device 10, 600. In the illustrated embodiment, the shelving system 100 includes two columns of shelves 106a and 106b. One column of shelves 106a is aligned along a right vertical axis 110a, adjacent to the right side 18 of the machine, with each shelf 102 extending at least partially along a right horizontal axis 112a from the front 14 to the rear 16 of the device 10. Another column of shelves 106b is aligned along a left vertical axis 110b, adjacent to the left side 20 of the device, with each shelf 102 extending at least partially along a left horizontal axis 112b from the front 14 to the rear 16 of the device 10, 600.

Between the two columns of shelves 106a and 106b is a column of space 114 without shelves. In alternate embodiments, the shelving system 100 can include one column of shelves 106 or three or more columns of shelves 106, and/or no column of space 114 without shelves or more than one column of space 114 without shelves 102. Further, the shelving system 100 includes a vertical distance 120 between shelves 102. As illustrated, the vertical distance 120 between shelves 102 can be varied. In the embodiment of FIG. 5, the vertical distances 120 between shelves 102 are varied from about thirteen inches near the bottom 24 of the device 10 to about three inches near the top 22 of the device 10, 600. In alternate embodiments, the vertical distances 120 can be varied in other proportions, the vertical distances 120 can be the same from top 22 to bottom 24 of the device 10, and/or the vertical distances 120 between shelves 102 can be varied for different columns of shelves 106.

As shown in FIG. 5, each shelf 102 has a width 122 extending at least partially along a horizontal axis 124. The horizontal axis 124 extends from the right side 18 to the left side 20 of the device 10, 600. One column of shelves 106a has a width 122a of about four inches, the other column of shelves 106b has a width 122b of about three inches, and the column of space 114 has a width 122c of about six inches. However, the width 122 of the shelves 102 can be the same for each column of shelves 106a and 106b, greater for the right column of shelves 106a than the left column of shelves 106b, greater for the left column of shelves 106b than the right column of shelves 106a, and/or varied from the bottom 24 to the top 22 of one or both columns of shelves 106a, 106b. The width 122c of the column of space 114 can be varied to be greater than the width 122a, 122b of one or more of the columns 106a, 106b, less than the width 122a, 122b of one or more of the columns 106a, 106b, or the same as the width 122a, 122b of one or more of the columns 106a, 106b.

In other embodiments, the shelf height is fully adjustable. That is, depending on applications and stock items, the shelf height can be customized so that, for example, oversized stock items and/or other unique packages can be stored efficiently. As another example, the shelf height can be adjusted to accommodate bottles placed on their sides. As described hereinafter, storing a bottle on its side allows the device 10, 600 to increase its storage capacity, in some cases.

Figure 6:
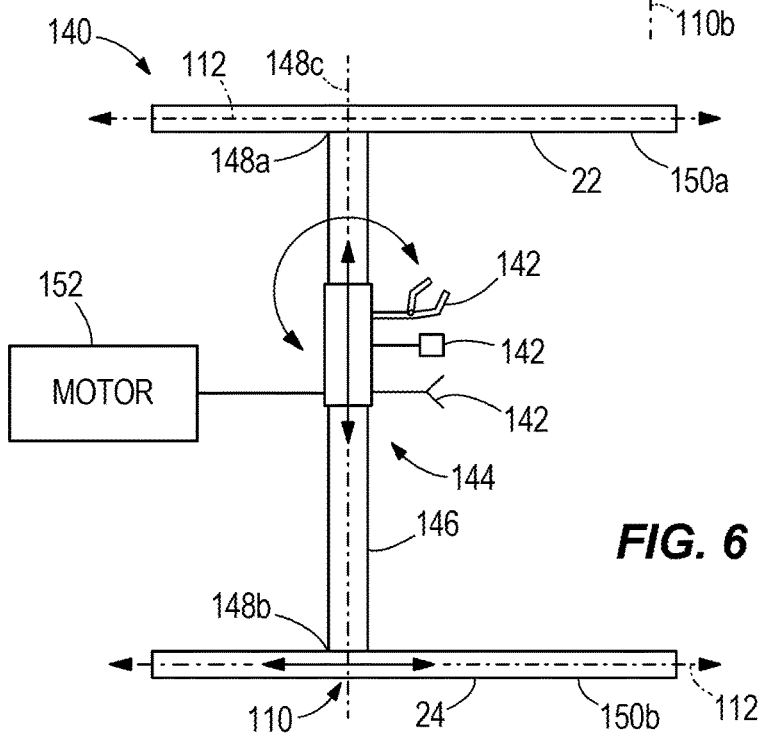
FIG. 6 is a side view of a transfer mechanism for the pharmaceutical storage and retrieval device.
Figure 7:
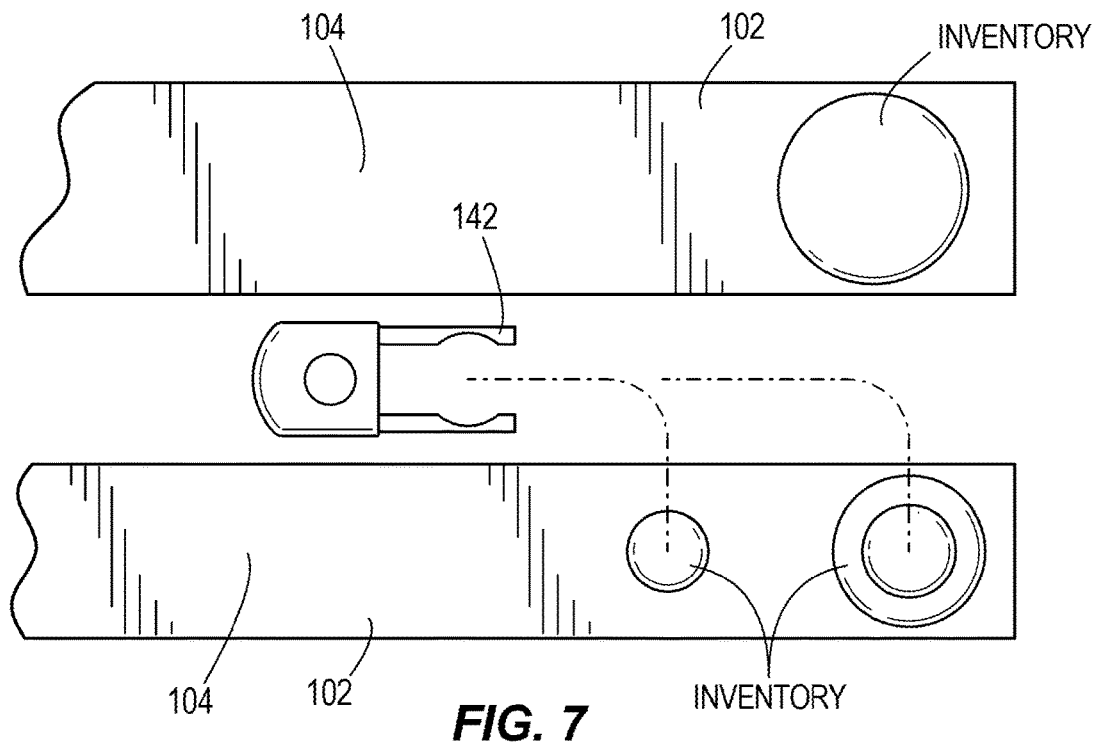
FIG. 7 is a top view of a portion of the interior of the pharmaceutical storage and retrieval device.

As illustrated in FIG. 6, the pharmaceutical storage and retrieval device 10, 600 includes a traveler mechanism 140 moveable along the axes 110, 112 for movement of inventory items therewith. The traveler mechanism 140 includes a carrying device 142 coupled to a robotic arm 144. The robotic arm 144 is located in the column of space 114 between shelves 102. As illustrated in FIG. 6, the traveler mechanism 140 can include one or more carrying devices 142. The carrying device 142, illustrated in the embodiment of FIG. 7, is a double bar picker, however in alternate embodiments, the carrying device 142 can be a head clamp, a suction cup, a hook, a shovel, etc., or any combination thereof, examples of which are shown in FIG. 6.

The robotic arm 144 of FIG. 6 includes an elongated portion 146. In the illustrated embodiment, the elongated portion 146 of the robotic arm 144 is in the form of a bar that extends generally from the top 22 of the device 10, 600 to the bottom 24 along the vertical axis 110. The robotic arm 144 also includes ends 148a and 148b to the elongated portion 146, with an axis 148c extending between the upper end 148a and the lower end 148b. The ends 148a and 148b of the robotic arm elongated section 146 are moveably coupled to one or more crossbar(s) 150. In the illustrated embodiment, one crossbar 150a extends along the top 22 of the device 10, 600 parallel to the horizontal axis 112 and is coupled to the upper end 148a of the robotic arm 144, and another crossbar 150b extends along the bottom 24 of the device 10, 600, parallel to the horizontal axis 112 and is coupled to the lower end 148b of the robotic arm 144. With movement initiated by a motor 152 (e.g., a servo motor configured to receive commands/instructions to move the robotic arm 144 between start and end points), the robotic arm 144 can move along the length of the crossbars 150 parallel to the horizontal axis 112. The carrying device 142 moves along the length of the elongated portion 146 from the upper end 148a to the lower end 148b along the vertical axis 110. In some embodiments, the elongated portion 146 and the carrying device 142 can rotate about the axis 148c of the elongated portion 146. In alternate embodiments, the carrying device 142 rotates about the axis 148c of the elongated portion 146 with the elongated portion 146 remaining stationary with respect to the axis 148c, and can include an articulate joint around the axis 148c. In alternate embodiments, the traveler mechanism 140 can be configured differently. In some embodiments, the machine 10 can include more than one traveler mechanism 140, more than one robotic arm 144, or both.

Figure 8:
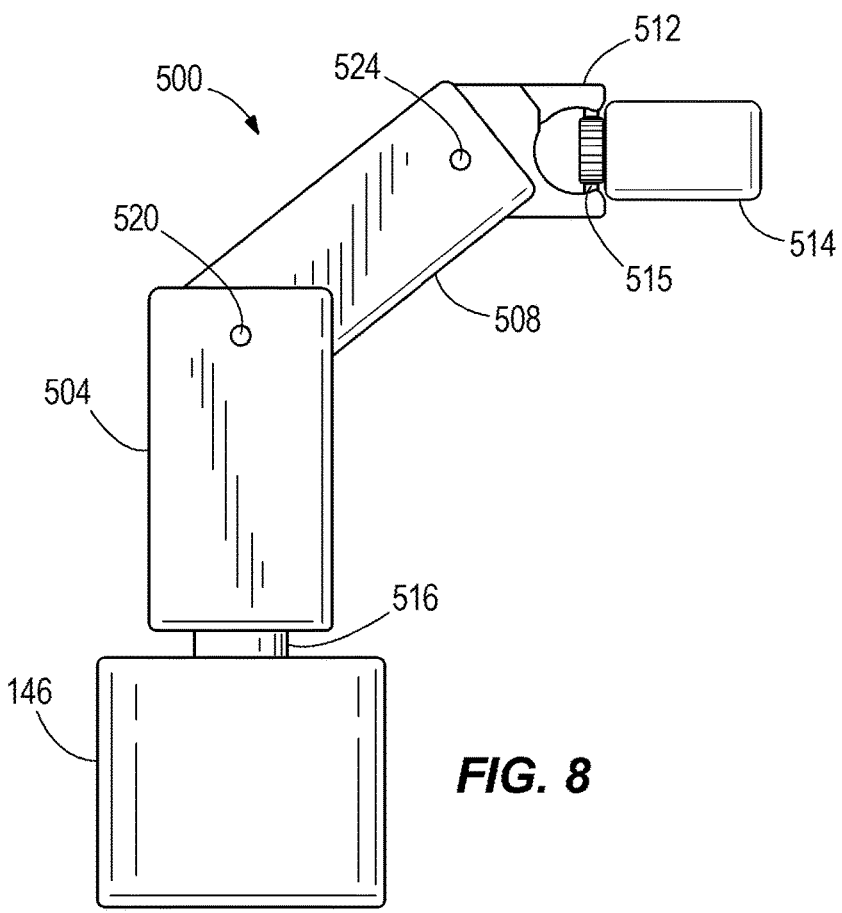
FIG. 8 is an alternate robotic arm for use with the pharmaceutical storage and retrieval device.

FIG. 8 shows a top view of a grabber 500 that can be used for the carrying device 142 as shown in FIG. 6. The grabber 500 includes an upper arm section 504, a fore arm section 508, and a grabbing section 512 for securing an exemplary bottle 514 at its cap 515, detailed hereinafter. Although FIG. 8 shows that the grabbing section 512 secures the exemplary bottle 514 at the cap 515, the grabbing section 512 can also be configured to grab other portions of the bottle 514, depending on the application and/or the orientation of the bottle.

In the embodiment shown, the upper arm section 504 is joined to the elongated portion 146 at joint 516, and to the fore arm section 508 at joint 520. The fore arm section 520 is joined to the grabbing section 512 at joint 524. As the elongated portion 146 moves with respect to axes 110 and 112 (of FIG. 6), the grabber 500, and specifically, the fore arm section 508 can rotate about joint 520, while the grabbing section 512 can rotate about joint 524. Thus, the grabber 500 allows for a plurality of coordinated motions, such as, forward and backward motions, up and down motions, and a plurality of translation motions. In this way, the grabber 500 has two degrees of freedom (DOF), and hence, minimizing the size or the width of the traveler mechanism 140. In other embodiments, the fore arm section 508 can have different shapes and sizes. In operation, the elongated portion 146 is moved to align the grabbing section 512 with a particular bottle. The grabbing section 512 then pulls the bottle 514 at its cap straight out of a storage or shelf slot, while the fore arm section 524 rotates about joint 520 and the elongated portion moves backwards. The elongated portion 146 then moves to align the bottle 514, the grabbing section 512, the fore arm section 508, and the upper arm section 504 with an access port, such as, the port 70. Thereafter, the elongated portion 146 moves forward to deliver the bottle 514 into the port 70.

Figure 9:
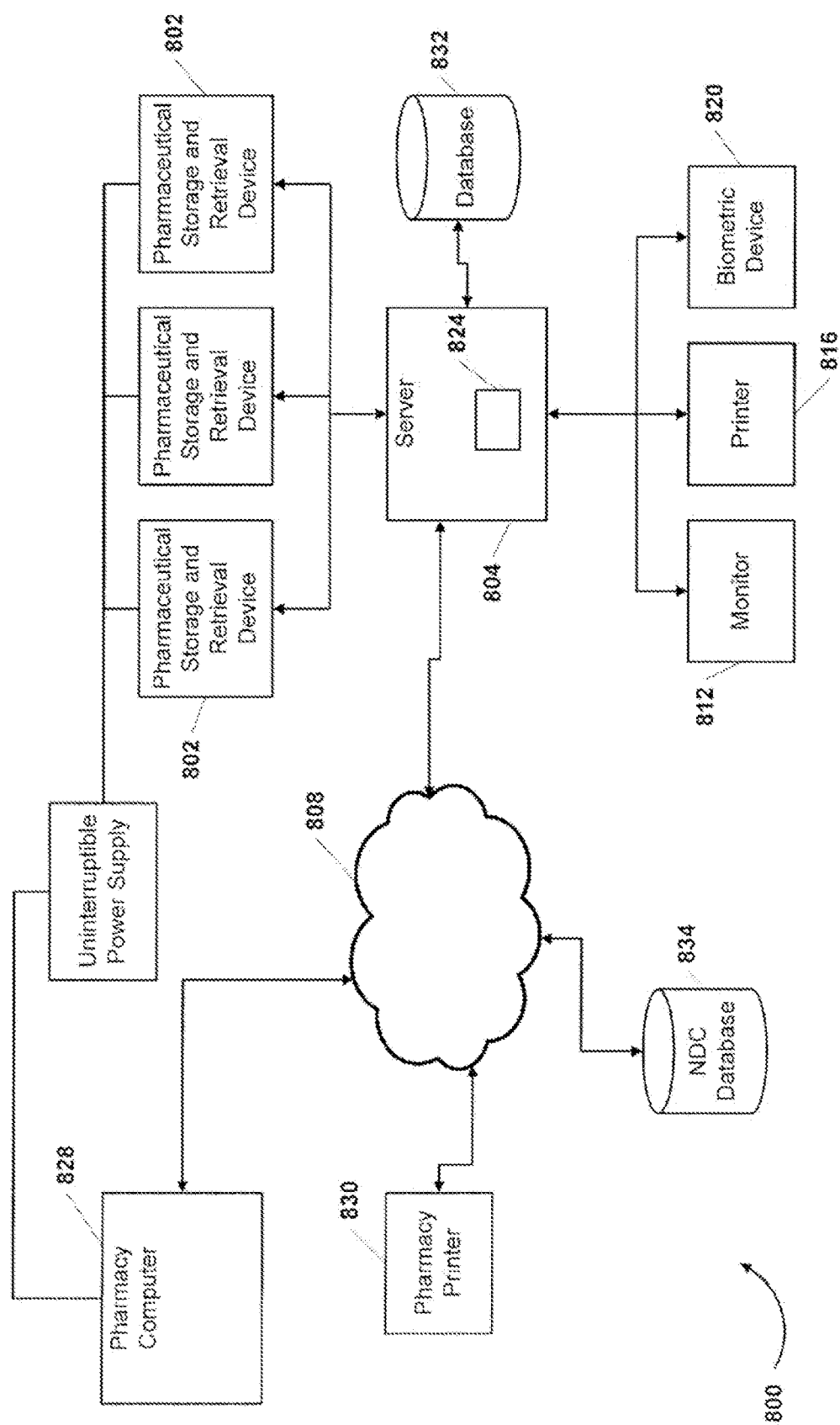
FIG. 9 is a schematic view of a pharmacy system implementing a pharmaceutical storage and retrieval device.

FIG. 9 illustrates a pharmacy system 800 according to one embodiment of the present invention. The pharmacy system 800 includes one or more pharmaceutical storage and retrieval devices 802. Although FIG. 9 illustrates three pharmaceutical storage and retrieval devices 802, it is noted that more or less devices can be utilized in a particular pharmacy. The device 802 can include similar components as the device 600 described above with respect to FIGS. 3-8.

The pharmacy system 800 also includes a server 804 in communication with the pharmaceutical storage and retrieval device 802, a network 808, a monitor 812 (e.g., with touch screen capability), a printer 816, and a biometric device 820. The server 804 includes an operating system for running various software programs and/or a communications application. In particular, the server 804 can include a software program(s) 824 that operates to communicate with the pharmaceutical storage and retrieval device 802 and to other devices and/or components on the network 808. The server 804 can include any suitable input/output device adapted to be accessed by pharmaceutical personnel. The server 804 can include typical hardware such as a processor, I/O interfaces, and storage devices or memory. The server 804 can also connect to and communicate with input devices such as a keyboard and a mouse. The server 804 can further connect to and communicate with standard output devices, such as the monitor 812. In addition, the server 804 can connect to and communicate with peripherals, such as the printer 816, the biometric device 820, and a scanner.

The server 804 can be networked with other servers 804 and pharmaceutical storage and retrieval devices 802. The other servers 804 may include additional and/or different computer programs and software and are not required to be identical to the server 804, described herein. The server 804 and pharmaceutical storage and retrieval device 802 can communicate with a pharmacy management system 828 over the network 808. The pharmacy management system 828 can communicate with a pharmacy printer 830 over the network 808 as well as with other devices and systems. The server 804 can also communicate with a database(s) 832 and/or other databases such as a National Drug Code database 834. It is noted that the software program(s) 824 could also reside on the pharmaceutical storage and retrieval device 802.

The network 804 can be built according to any suitable networking technology or topology or combinations of technologies and topologies and can include multiple sub-networks. Connections between the devices and systems shown in FIG. 9 can be made through local area networks ("LANs"), wide area networks ("WANs"), public switched telephone networks ("PSTNs"), wireless networks, Intranets, the Internet, or any other suitable networks. In a hospital or medical care facility, communication between the devices and systems shown in FIG. 9 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

The two-way arrows in FIG. 9 generally represent two-way communication and information transfer between the network 808 and other devices connected to the network 808. However, for some medical and computerized equipment, only one-way communication and information transfer may be necessary.

Figure 10:
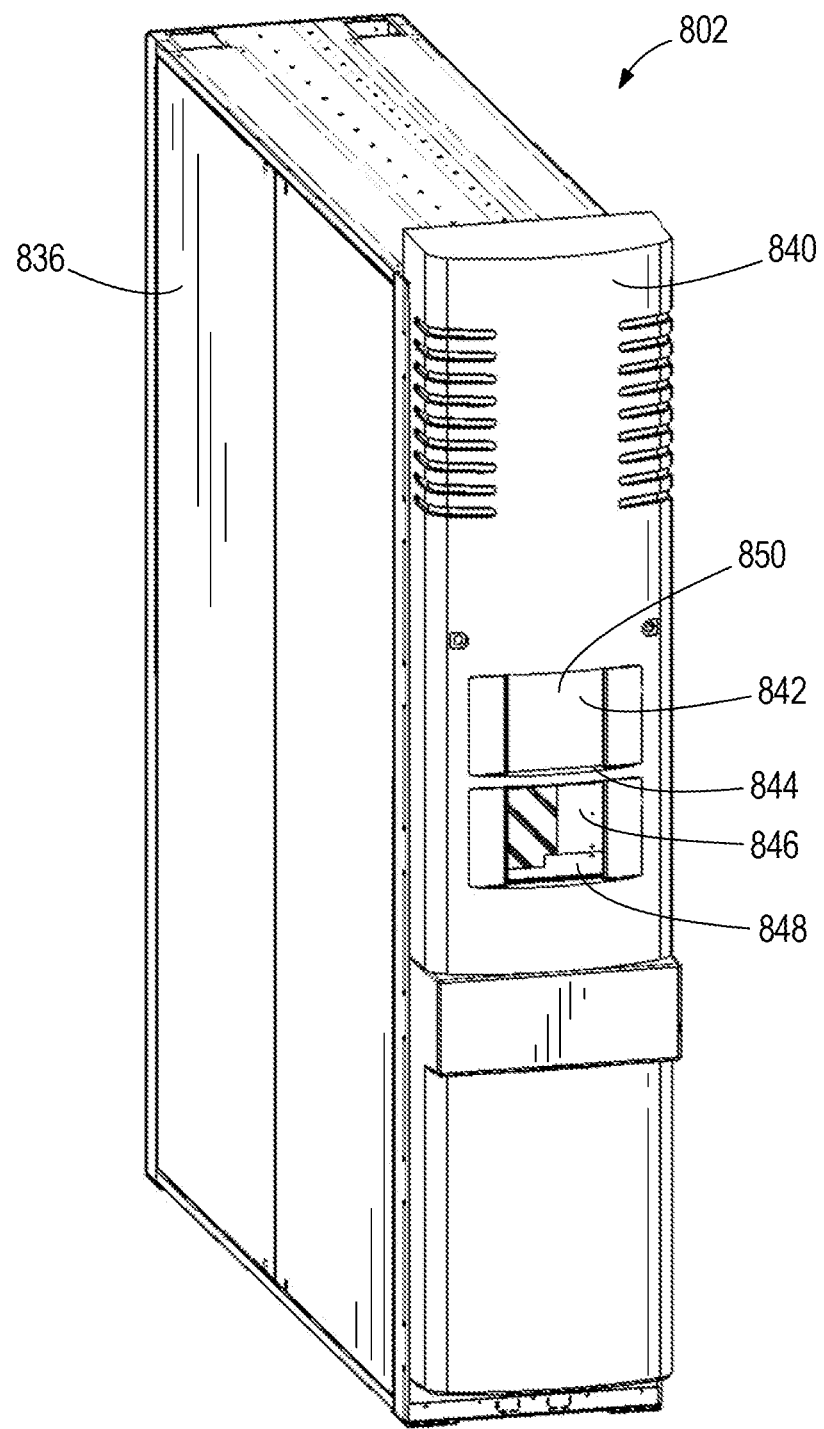
FIG. 10 is a perspective view of a pharmaceutical storage and retrieval device according to an embodiment of the present invention.
Figure 11:
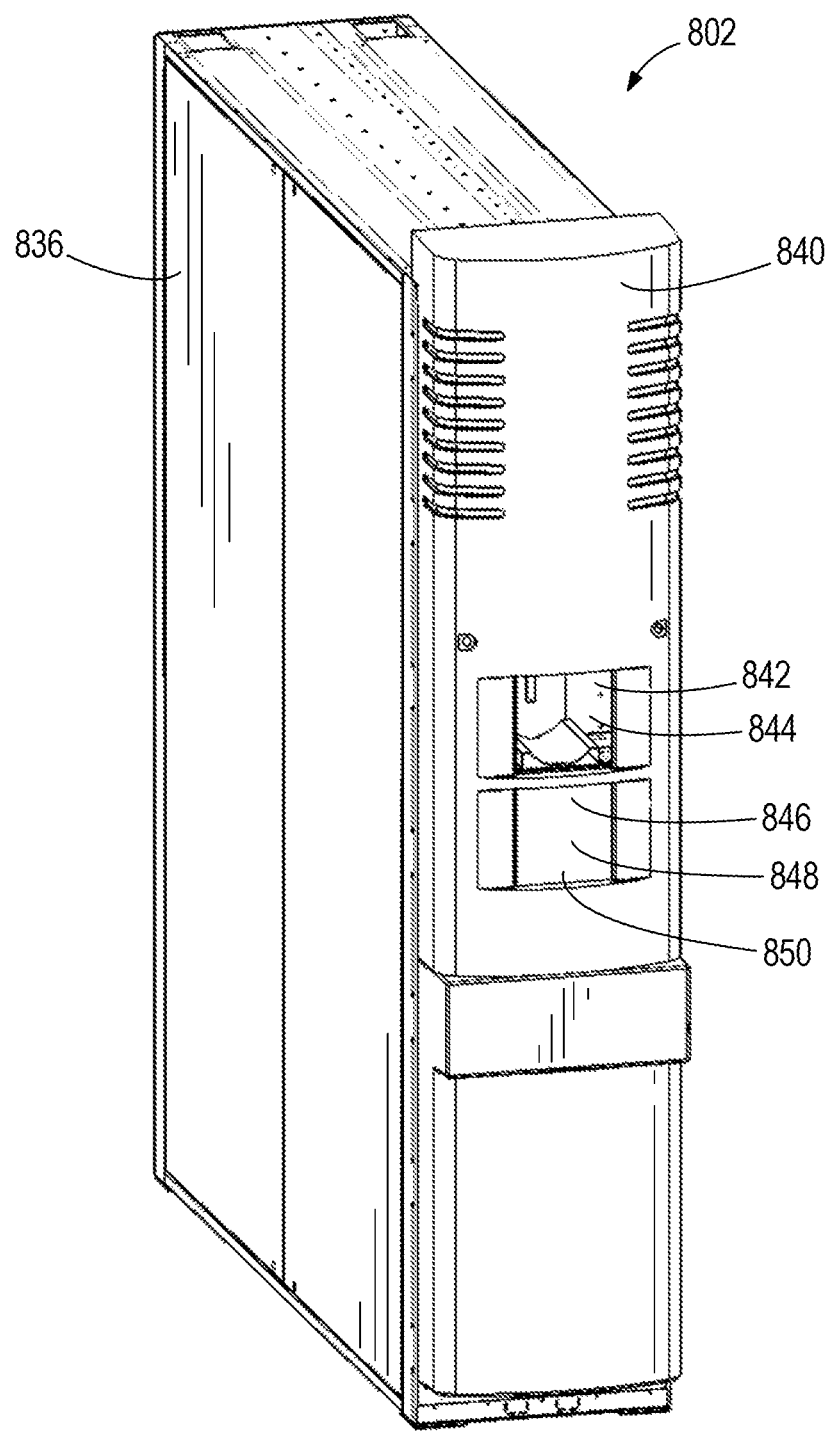
FIG. 11 is a perspective view of the pharmaceutical storage and retrieval device illustrated in FIG. 10.

FIGS. 10-23 illustrate the pharmaceutical storage and retrieval device 802 in more detail according to one embodiment of the present invention. The device 802 includes a housing 836 having a plurality of sides configured to enclose a gantry system 838. The housing 836 also includes a front panel 840 supporting a first port 842 having a first opening 844 and a second port 846 having a second opening 848. Additional or fewer ports are also possible in alternative constructions. The front panel 840 includes a door 850 moveable between a first position and a second position within the first opening 844 and the second opening 848 to provide access to the first port 842 and the second port 846. The door 850 can move in a vertical direction. The front panel also can include a second door where door 850 is dedicated to the first port 842 while the second door is dedicated to the second port 846. FIG. 10 illustrates the door 850 in a first position with a view to the interior of the second port 846 while access to the first port 842 is closed. FIG. 11 illustrates the door 850 in a second position with a view to the interior of the first port 842 while access to the second port 846 is closed.

Figure 12:
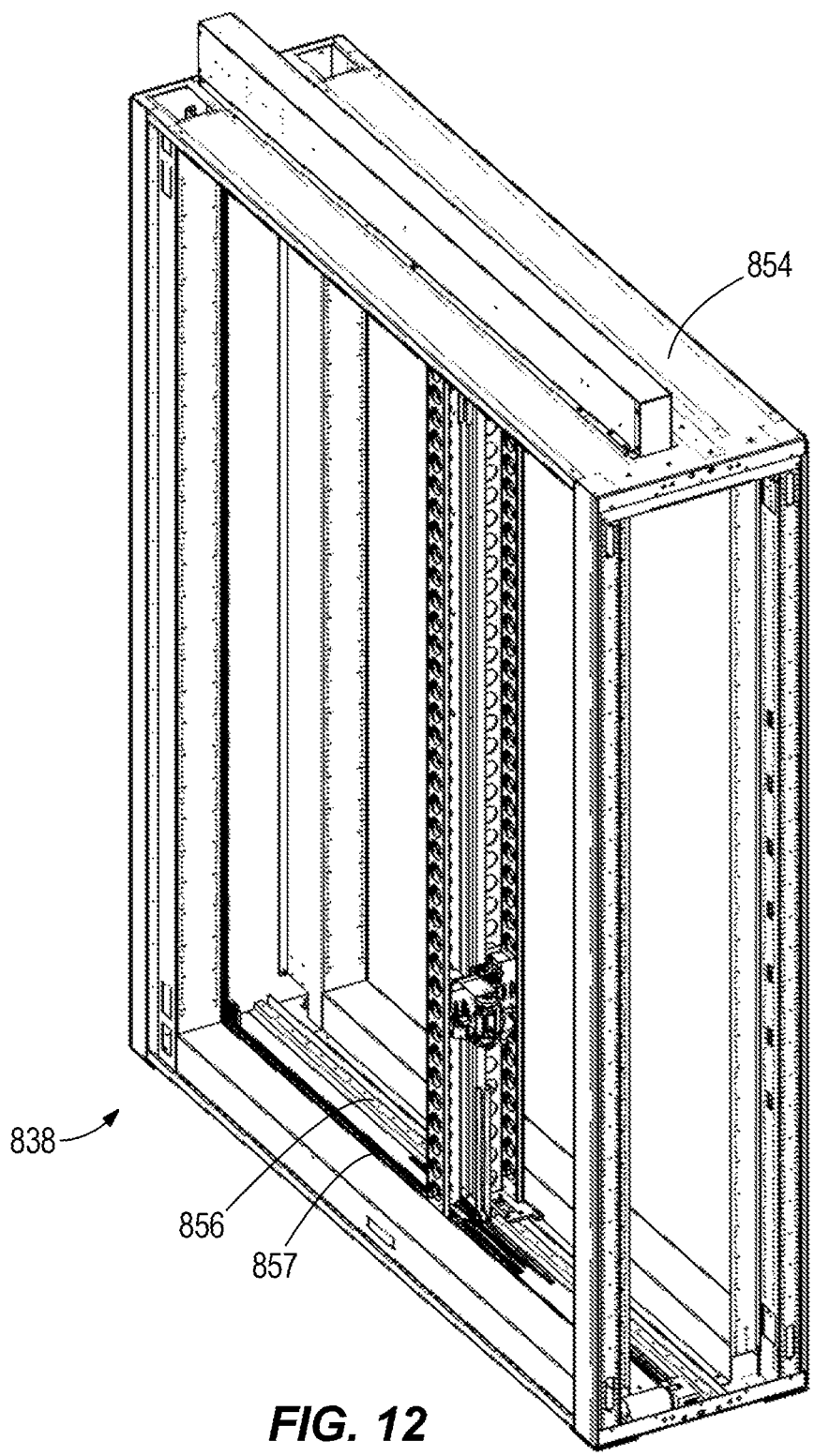
FIG. 12 is a perspective view of a gantry system of the pharmaceutical storage and retrieval device illustrated in FIG. 10.
Figure 13A:
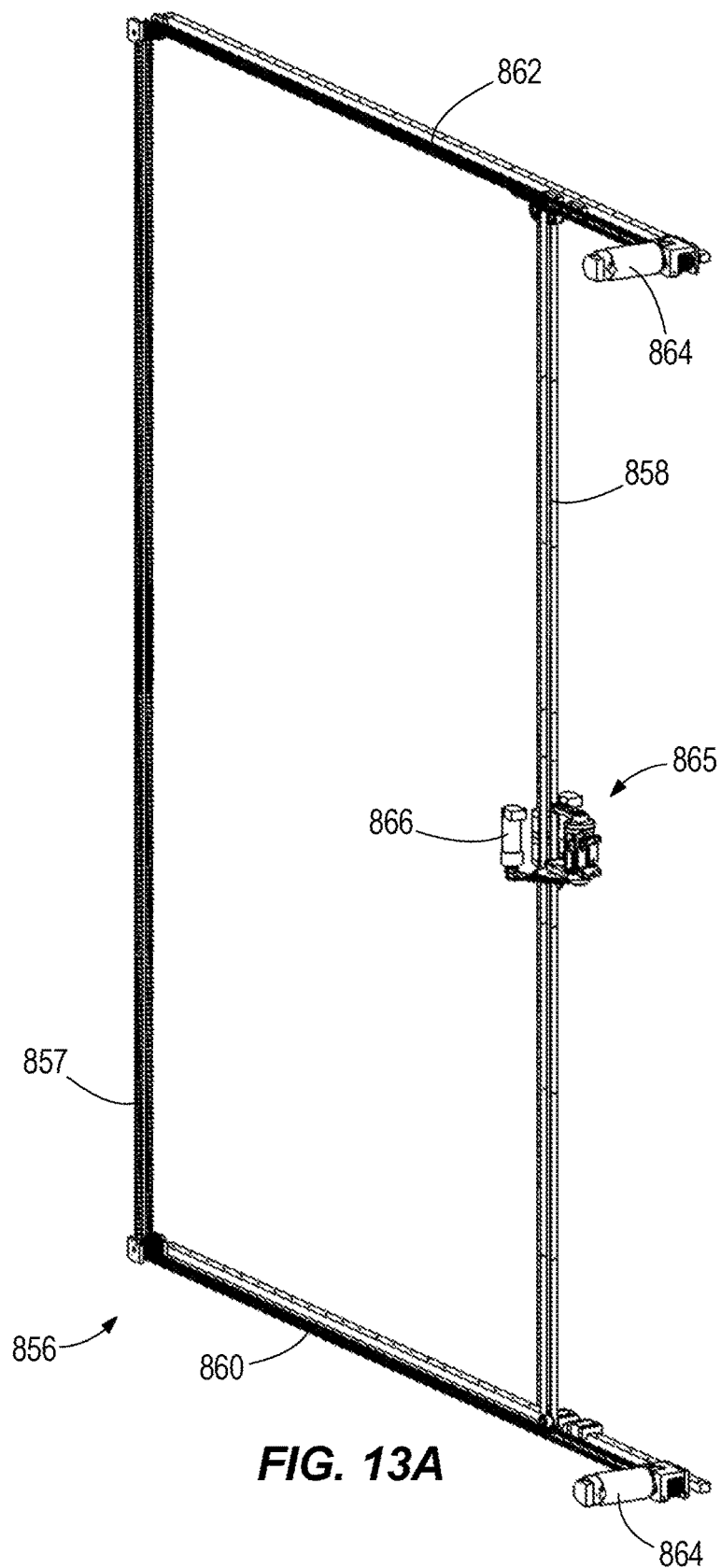
FIG. 13A is a perspective view of a track system of the pharmaceutical storage and retrieval device illustrated in FIG. 10.

FIGS. 12-13 illustrate the gantry system 838 supported by the housing 836. The gantry system 838 includes a frame 854 adapted to support a track system 856. The track system 856 includes a generally vertical track 858 having a first end and a second end, a first generally horizontal track 860 adapted to support one of the first end and the second end of the track 858, and a second generally horizontal track 862 adapted to support one of the first end and the second end of the track 858. The track 858 is configured to travel along the first horizontal track 860 and the second horizontal track 862.

Figure 13B:
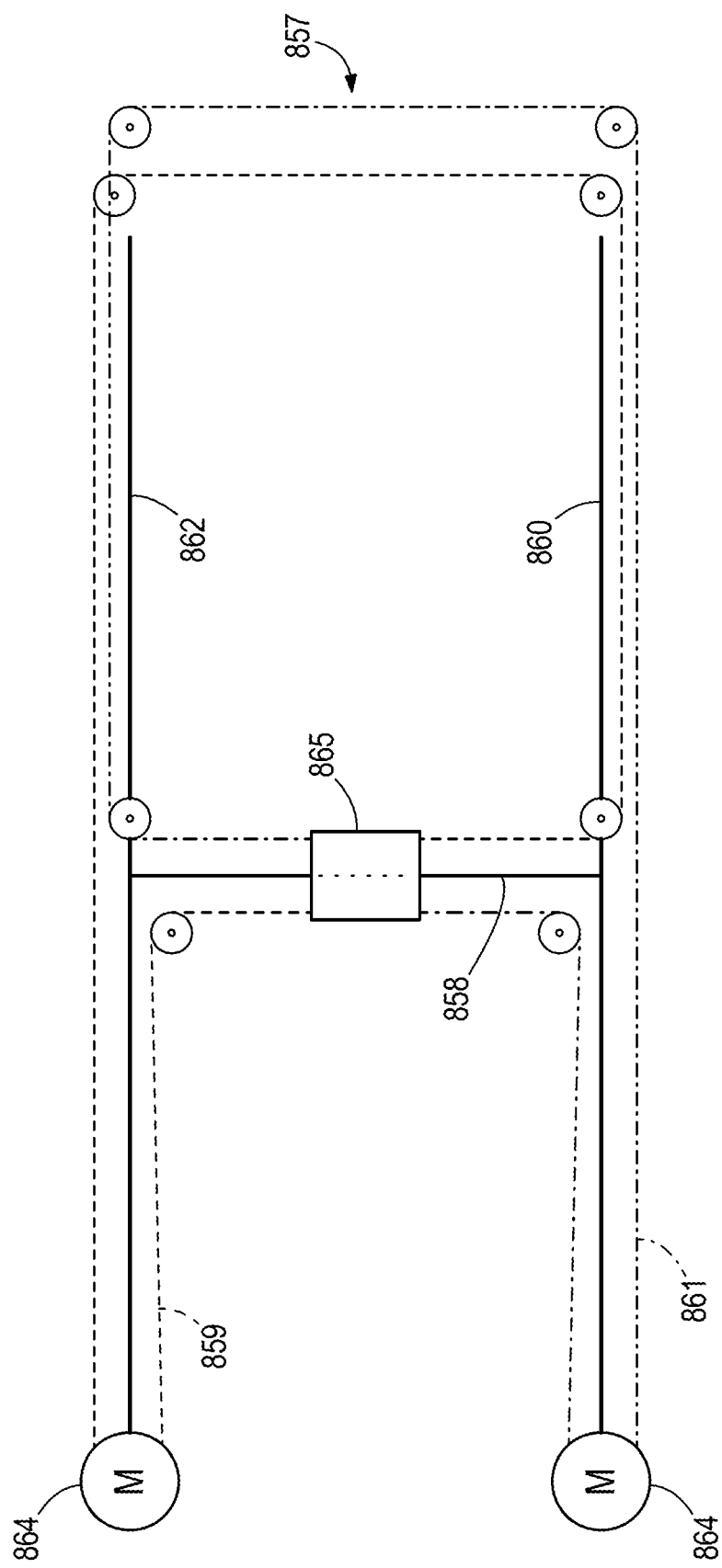
FIG. 13B is a schematic view of a belt system of the pharmaceutical storage and retrieval device illustrated in FIG. 10.

The gantry system 838 also includes a plurality of motors 864 operable to move the vertical track 858 along the horizontal tracks 860, 862. The motors 864 can be connected to a belt system 857 supported by the track system 856 that pulls one or more belts along the track system 856 to move the vertical track 858 along the horizontal tracks 860, 862. The motors 864 coordinate with one another to activate the belt system 857 to provide both horizontal and vertical motion. The belt system 857 includes a plurality of pulleys, a first belt circuit 859 and a second belt circuit 861 as illustrated in FIG. 13B. When both motors 864 rotate clockwise, a carriage system 865 (discussed below) moves in a downward direction along the vertical track 858. When both motors 864 rotate counter-clockwise, the carriage system 865 moves in an upward direction along the vertical track 858. When the motors 864 rotate in opposite directions, the vertical track 858 moves horizontally along the horizontal tracks 860, 862.

The gantry system 838 also includes a carriage system 865 operable to move along the vertical track 858. The carriage system 865 includes a first motor 866 operable to rotate a gripper assembly 872 (discussed below) about a first axis 867. The carriage system 865 also includes a second motor 869 operable to rotate the gripper assembly 872 about a second axis 871. The motors 866, 869 provide coordinated motion of the gripper assembly 872 to retrieve, position, and transport a bottle between a shelf location and the ports 842, 846. The coordinated motion reduces the amount of space within the device 802 due to the reduced arc motion of the bottle as the gripper assembly 872 retrieves and positions the bottle from its shelf location.

Figure 14:
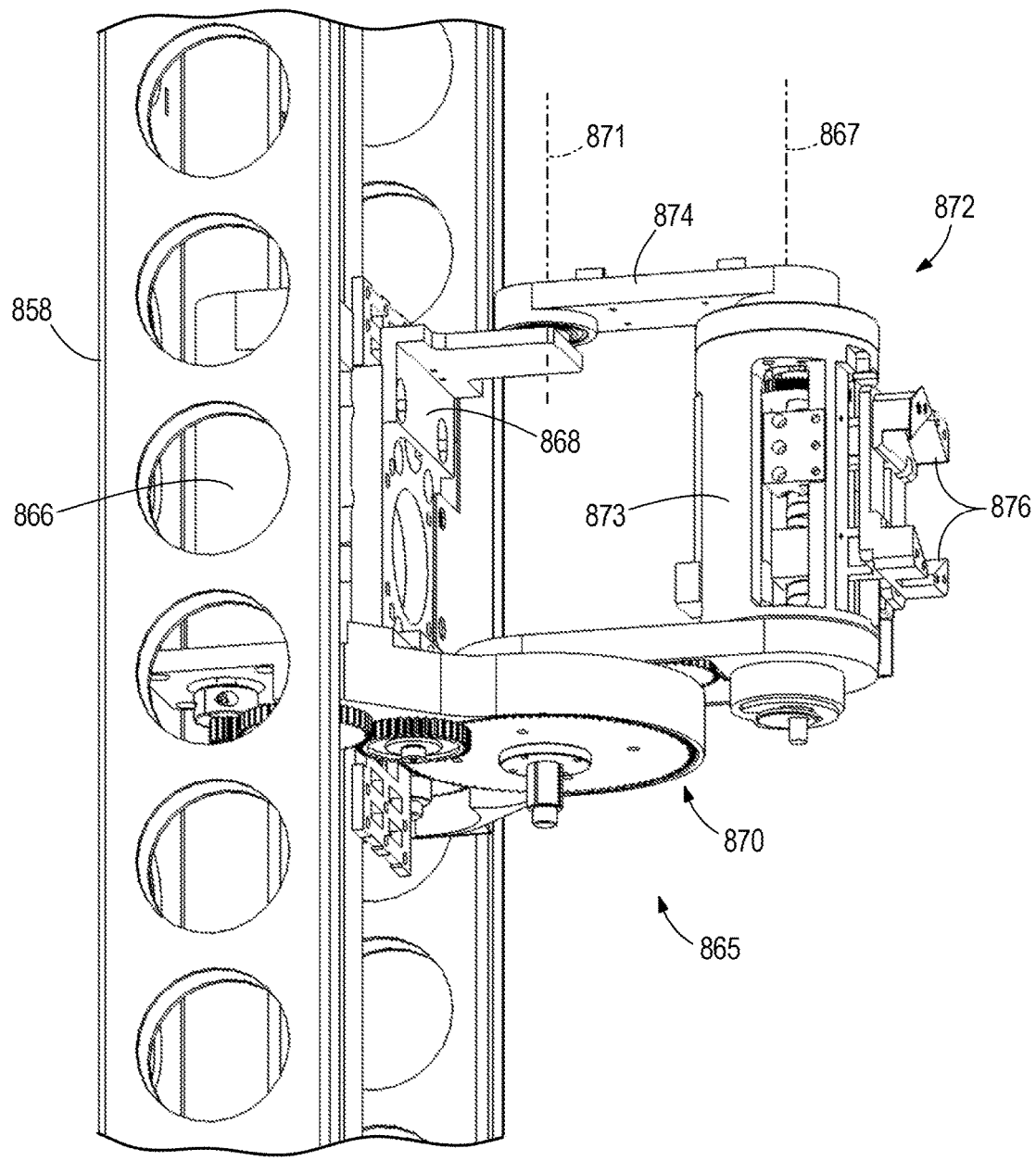
FIG. 14 is a perspective view of a carriage system of the pharmaceutical storage and retrieval device illustrated in FIG. 10.
Figure 15:
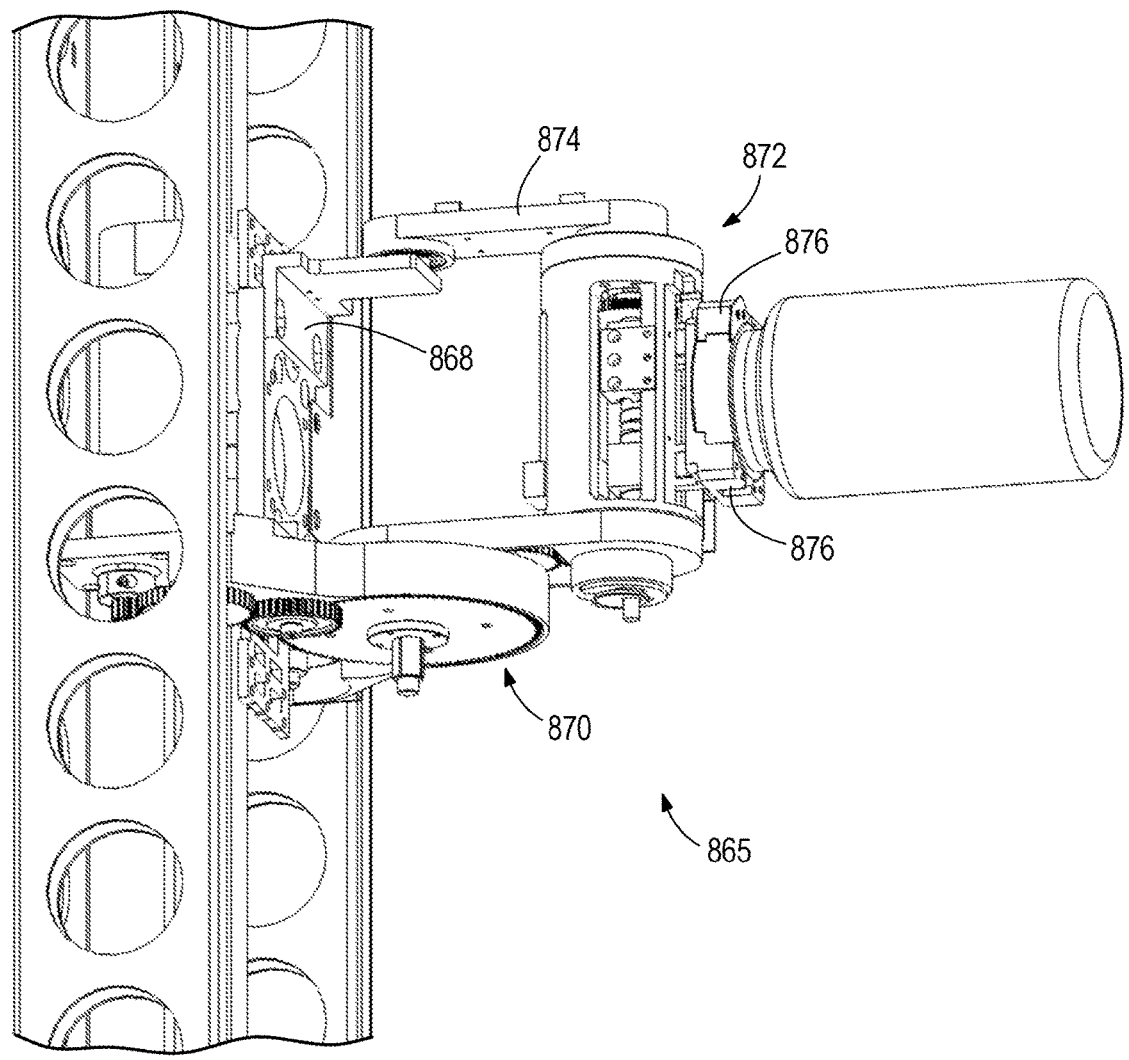
FIG. 15 is a perspective view of a carriage system of the pharmaceutical storage and retrieval device illustrated in FIG. 10.
Figure 16:
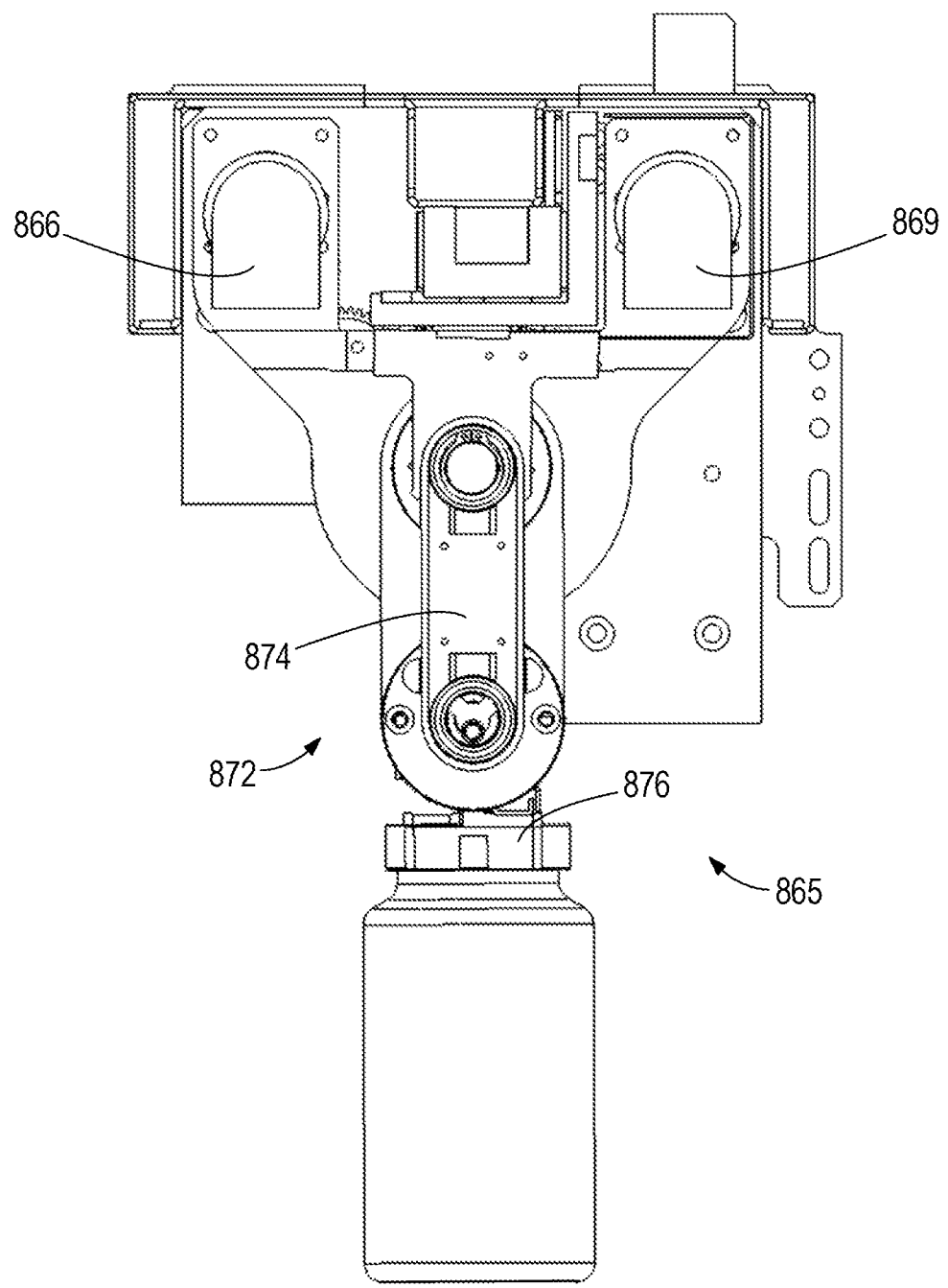
FIG. 16 is a top view of a carriage system of the pharmaceutical storage and retrieval device illustrated in FIG. 10.
Figure 17:
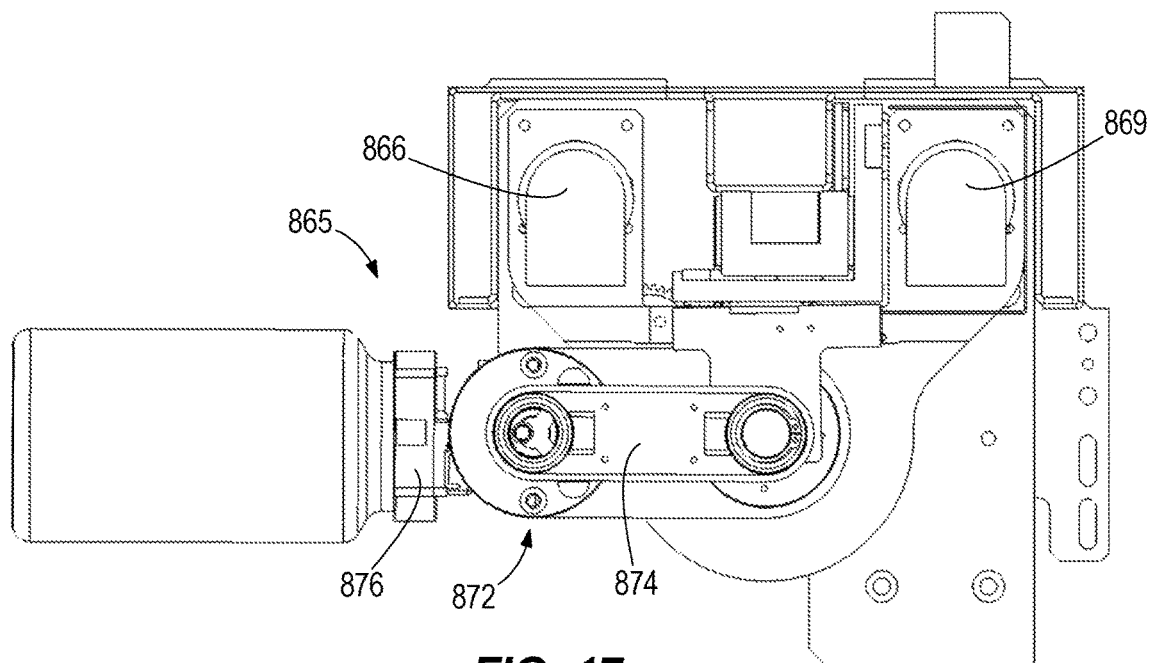
FIG. 17 is a top view of a carriage system of the pharmaceutical storage and retrieval device illustrated in FIG. 10.
Figure 18:
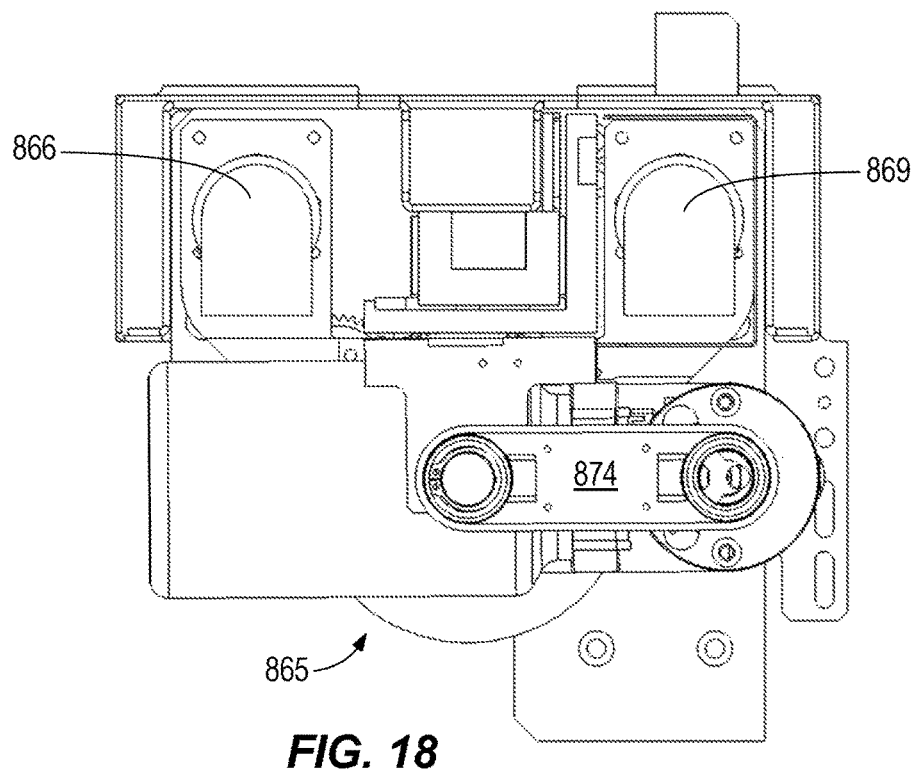
FIG. 18 is a top view of a carriage system of the pharmaceutical storage and retrieval device illustrated in FIG. 10.

The carriage system 865, illustrated in FIGS. 14-18, includes a frame 868 adapted to support a gear assembly 870 and a gripper assembly 872. The gear assembly 870 is coupled to the motors 866, 869 and includes a plurality of gears operable to rotate the gripper assembly 872 between a plurality of positions. The gripper assembly 872 includes a support member 874 pivotably coupled to the frame 868. The gripper assembly 872 also includes a motor 873 to move a plurality of fingers 876, which are operable to move between a first position and a second position to grip a bottle. FIG. 14 illustrates the carriage system 865 without the gripper assembly 872 holding a bottle. FIGS. 15-18 illustrate the carriage system 865 with the gripper assembly 872 holding a bottle. As illustrated in FIG. 15, the fingers 876 of the gripper assembly 872 grip the bottle cap however it is noted that the fingers 876 can grip the bottle at locations other than the cap. FIGS. 16-18 illustrate motion of the gripper assembly 872 through a series of steps in gripping a bottle. FIG. 16 illustrates the gripper assembly 872 in a first position gripping a bottle just retrieved from (or about to be positioned in) a particular location within the device 802. FIG. 17 illustrates the gripper assembly 872 in a second position (generally rotated about 90 degrees from the first position). FIG. 18 illustrates the gripper assembly 872 in a third position translated along a plane defined by the second position and a predetermined distance from the second position.

While the gripper assembly 872 is in the third position, the carriage system 865 is operable to move along the vertical track 858, and the vertical track 858 is operable to move along the horizontal tracks 860, 862. It is noted that the gripper assembly 872 may be in other positions other that those illustrated in the figures when the carriage system 865 moves.

Figure 19:
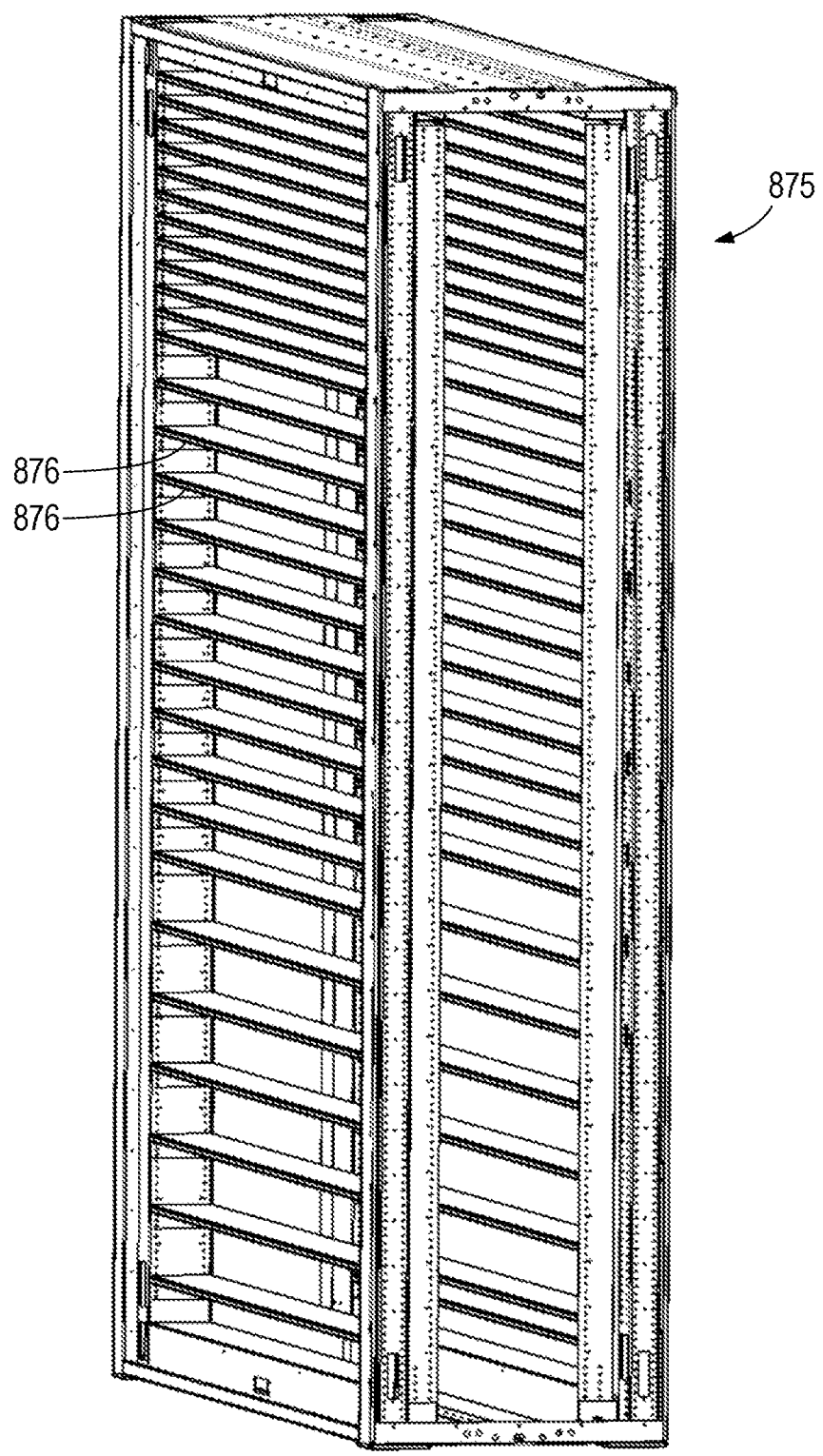
FIG. 19 is a perspective view of a shelving system of the pharmaceutical storage and retrieval device illustrated in FIG. 10.

With reference to FIG. 19, the device 802 includes a shelving system 875 supported by the housing 836. The shelving system 875 includes a plurality of generally horizontally oriented shelves 876 positioned along a vertically-oriented plane. The shelves 876 are positioned a predetermined distance apart where the distances can vary to be able to accommodate multiple sized bottles.

Figure 20:
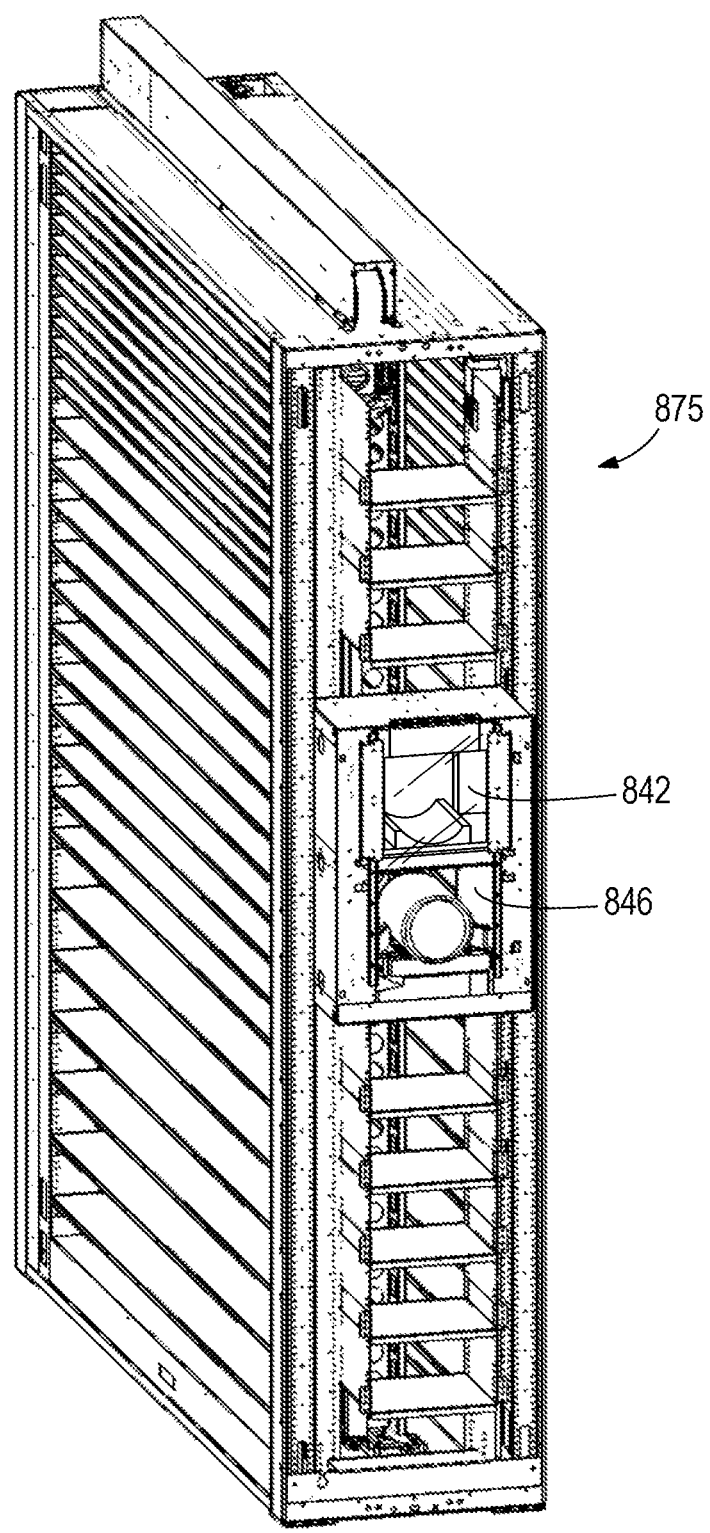
FIG. 20 is a perspective view of the shelving system of the pharmaceutical storage and retrieval device illustrated in FIG. 10.
Figure 21:
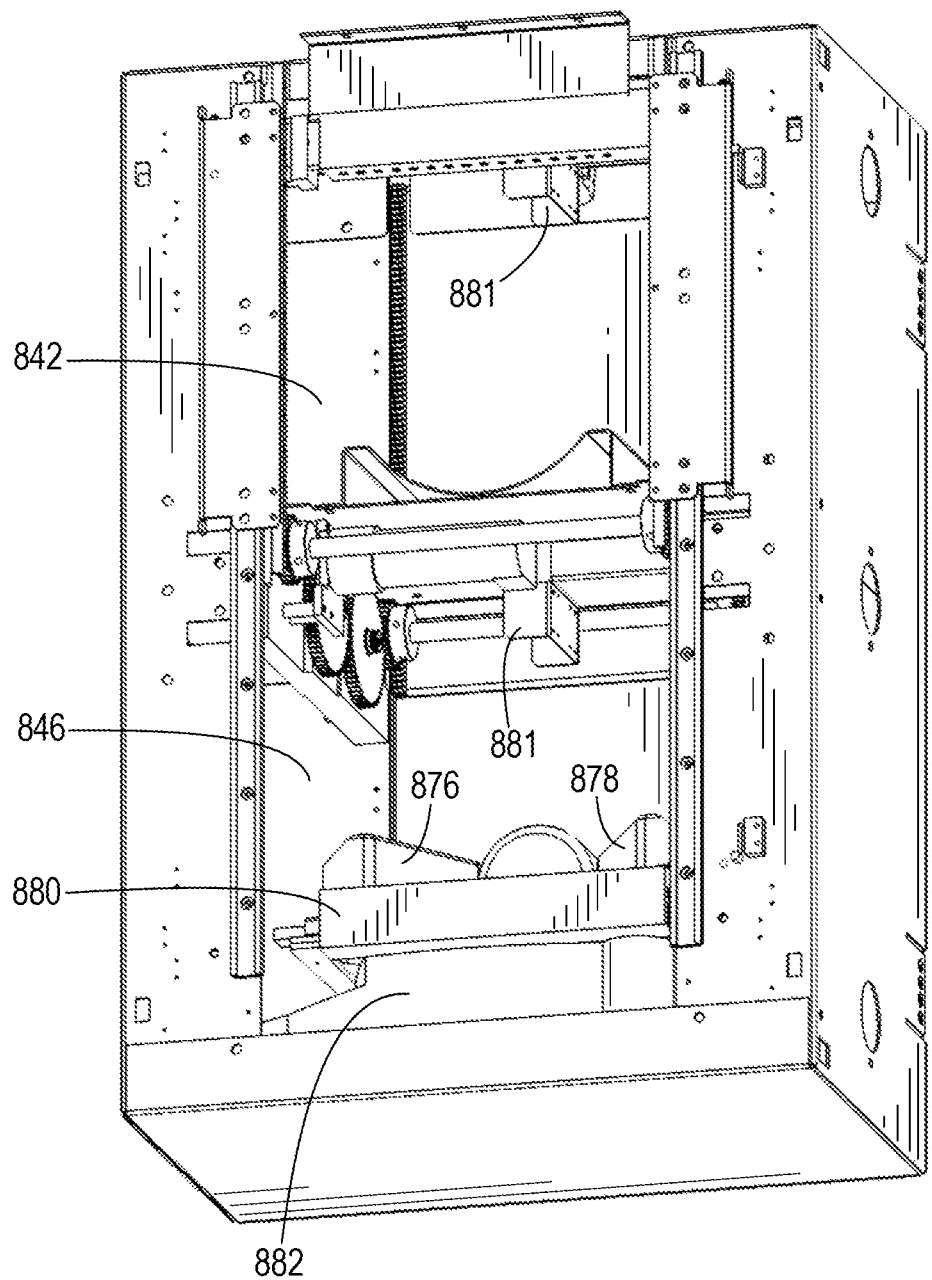
FIG. 21 is a perspective view of a first port and a second port of the pharmaceutical storage and retrieval device illustrated in FIG. 10.
Figure 22:
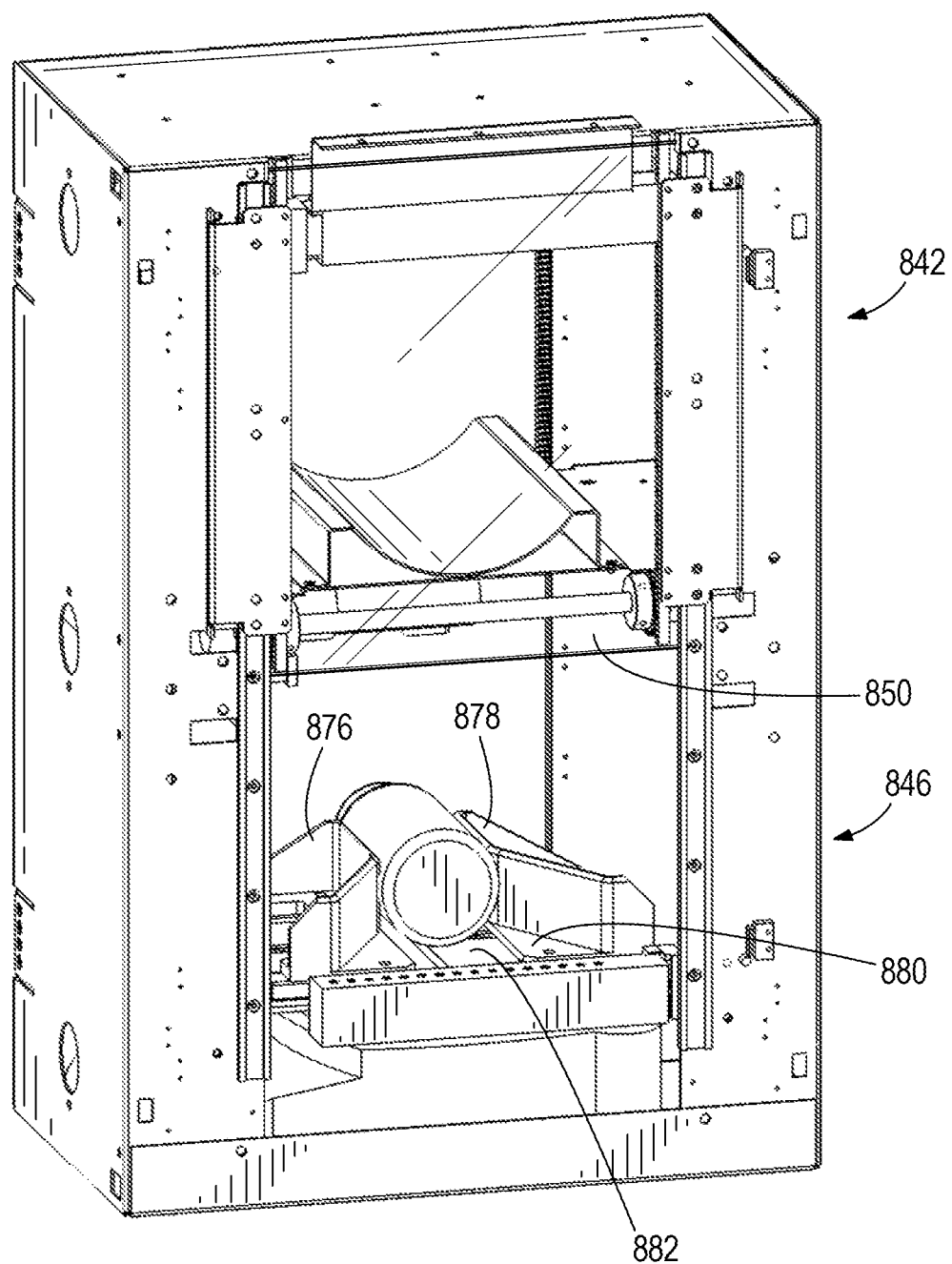
FIG. 22 is a perspective view of a first port and a second port of the pharmaceutical storage and retrieval device illustrated in FIG. 10.
Figure 23:
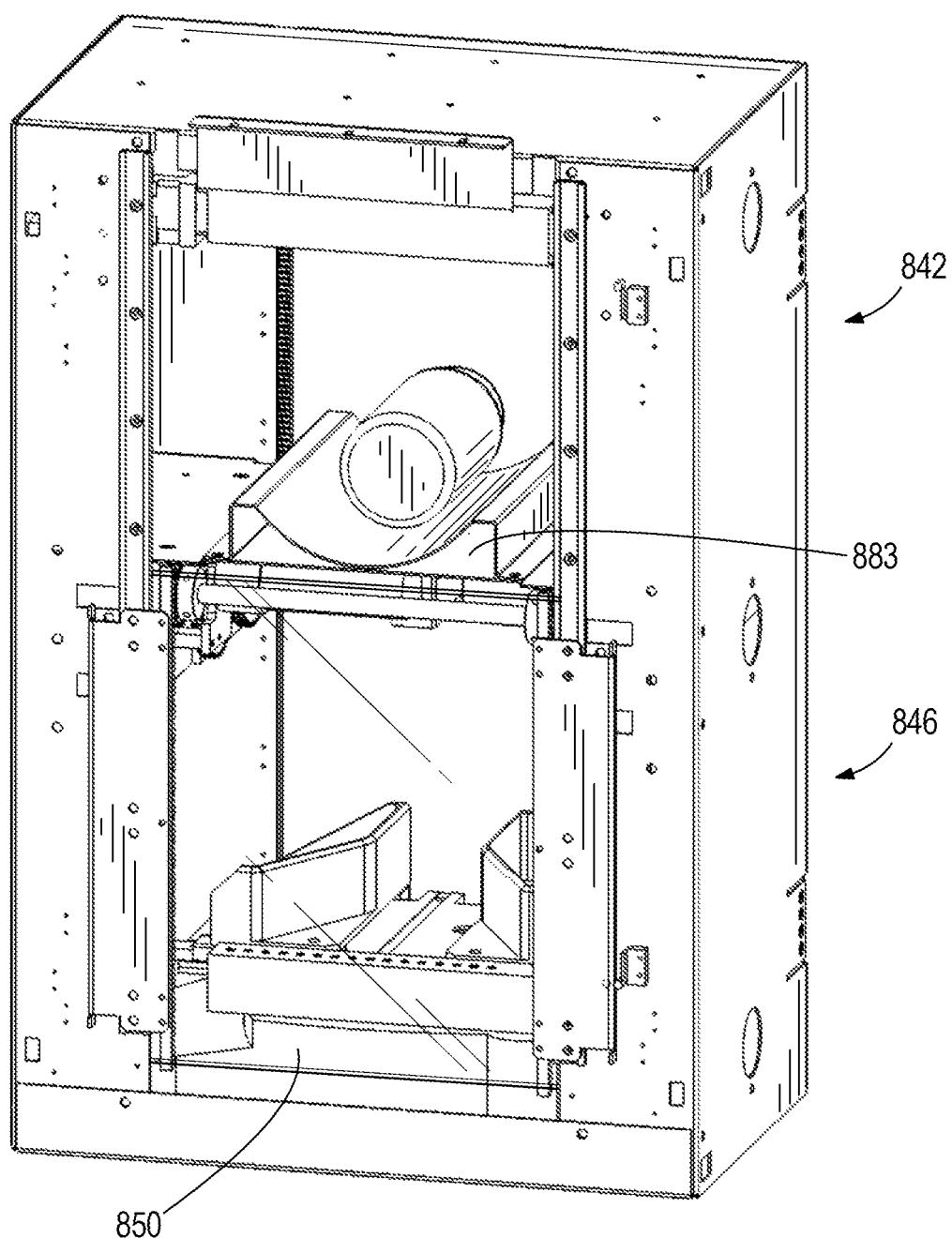
FIG. 23 is a perspective view of a first port and a second port of the pharmaceutical storage and retrieval device illustrated in FIG. 10.

FIG. 20 illustrates the first port 842 and the second port 846 supported by the frame in relation to the shelving system 875. FIG. 20 further illustrates a bottle positioned within the second port 846 while access to the first port 842 is closed. FIGS. 21-23 further illustrate the first port 842 and the second port 846 in more detail. The second port 846 includes a bottle positioned on its side between a first member 876 and a second member 878. The first member 876 and the second member 878 are operable to slide along a platform 880, which supports the bottle. The position of the first member 876 and the second member 878 can determine a size of the bottle. The platform 880 can include a scanner 881 (or other image acquisition device) operable to read a label on the bottle and to acquire an image of the bottle dimensions and a scale 882 operable to measure a weight of the bottle while supported on the platform 880. The door 850 covers the first port 842 to prevent access to the first port while access to the second port 846 is allowed. Generally, a user is performing a stocking or returning operation when access to the second port 846 is allowed.

FIG. 23 illustrates the first port 842 including a support 883 having a generally concave surface to support a bottle. Generally, a user is performing a retrieval or dispensing operation when access to the first port 842 is allowed.

Figure 24:
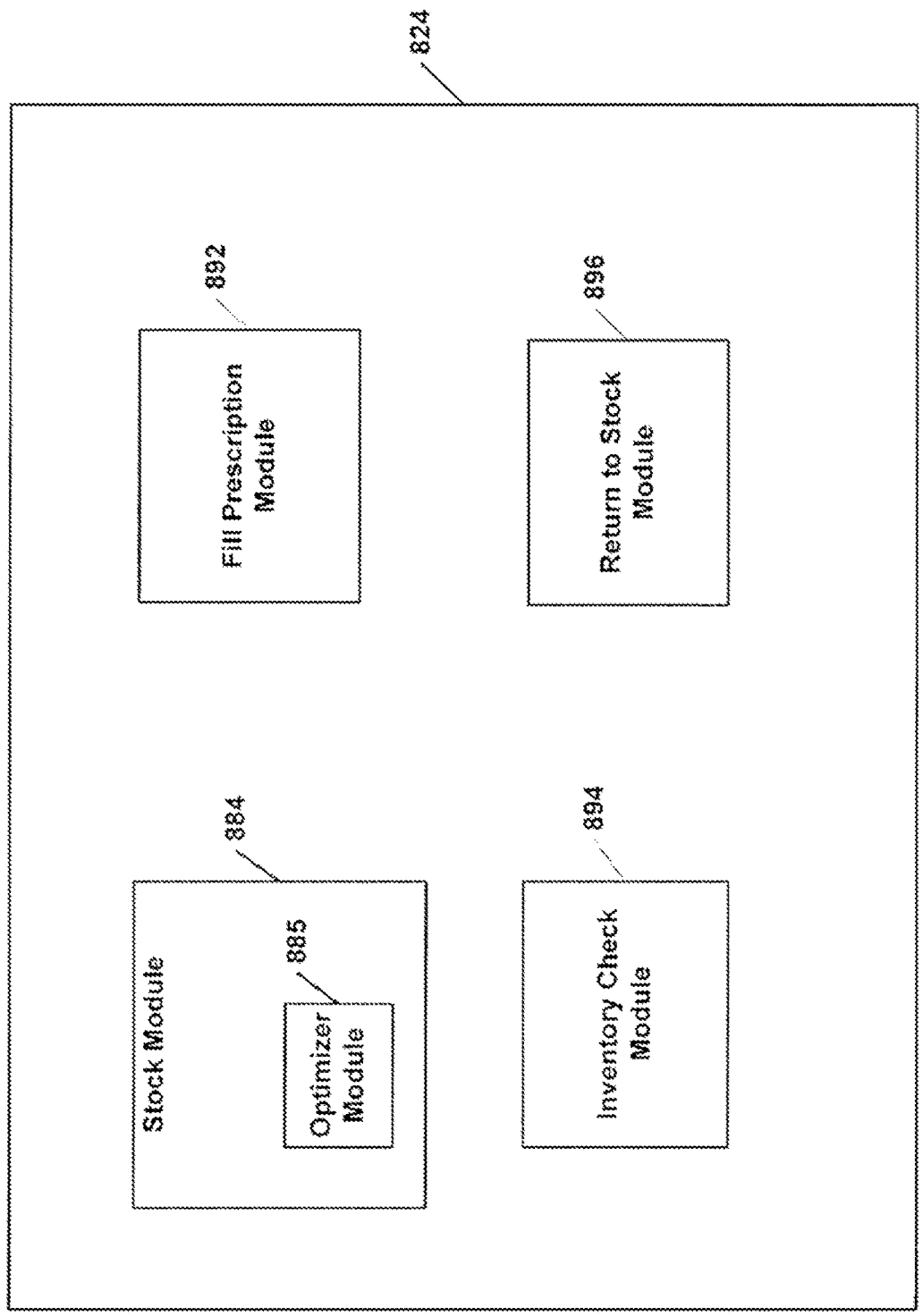
FIG. 24 is a block diagram illustrating a software program for controlling the pharmaceutical storage and retrieval device.

The software program 824 illustrated in FIG. 24 includes a plurality of modules accessible by pharmacy personnel to perform functions of the pharmaceutical storage and retrieval device 802. The software program 824 includes a stock module 884 operable to provide instructions to the pharmaceutical storage and retrieval device 802 to receive a bottle, grab the bottle, and position the bottle on a shelf within the device 802. The stock module 884 also is operable to maintain an inventory list of the bottles being input to the device 802. The inventory list can assist pharmacy personnel in reporting discrepancies between orders and what was received. The stock module 884 also can generate inventory and/or restocking requests that the server 804 can transmit to an appropriate system via the network 808.

The stock module 884 also instructs the device 802 to read or scan a National Drug Code (NDC) barcode label on the bottle and to store the read data in the server 804 and/or database 832. The NDC database 834 includes data such as manufacturer, type of drug, count, and type of package. The bottles being stocked remain in the original manufacturer package. This read data can be associated with a particular location within the device 802 based on where the bottle is specifically located.

Figure 25:
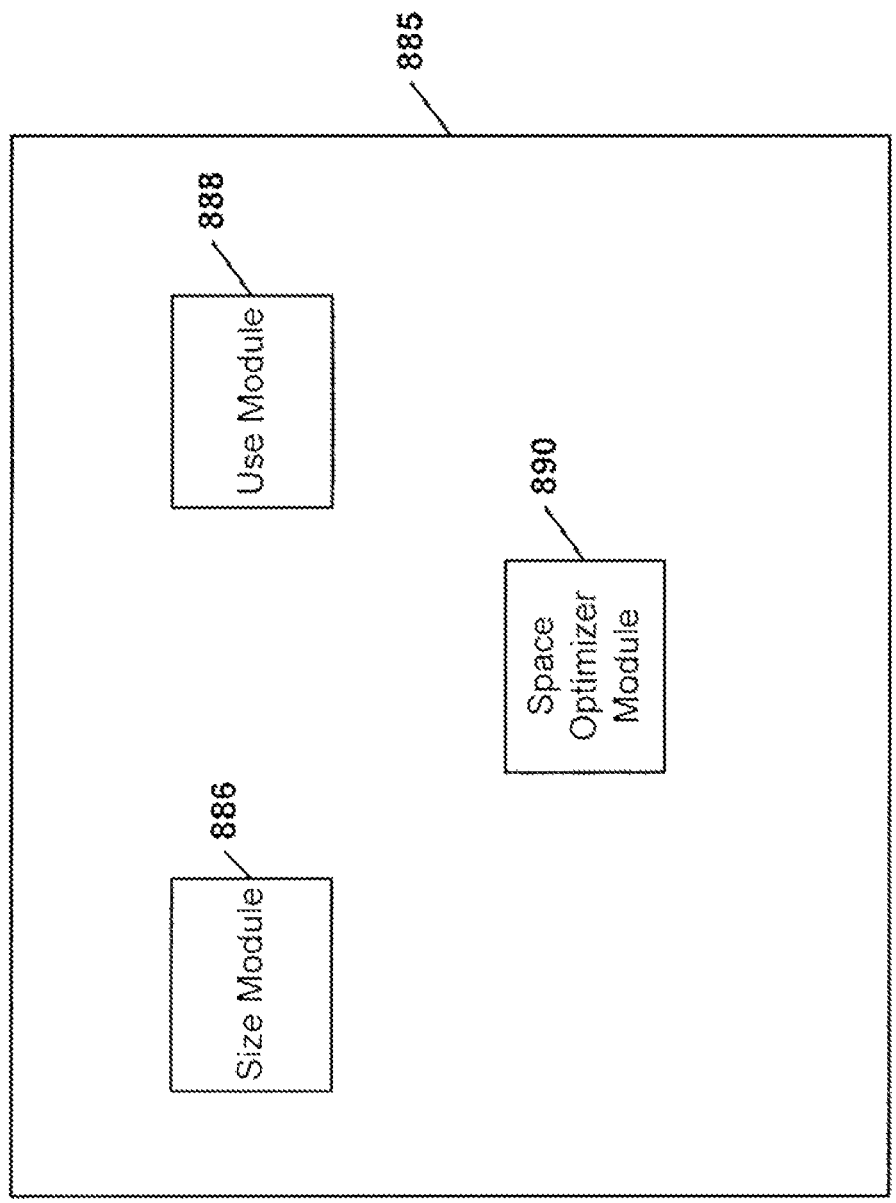
FIG. 25 is a block diagram illustrating a software program for controlling the pharmaceutical storage and retrieval device

The stock module 884 includes an optimizer program 885 operable to determine an optimal location for the bottle being received in the device 802. The optimizer program 885, illustrated in FIG. 25, includes a size module 886 operable to instruct the scanner 826 within the second port 846 to obtain an image of the bottle. The size module 886 is operable to determine a cap diameter, a bottle shape, and a bottle size (e.g., height and width) based on the acquired image. Alternatively, the size module 886 can access the NDC database 834 or other database for the size information of the bottle. The optimizer program 885 also includes a use module 888 operable to determine how frequently the pharmacy utilizes the particular medication. The use module 888 can access the database 832 for data or request information from the pharmacy management system 828 on how frequently the particular medication is utilized.

The optimizer program 885 also includes a space optimizer module 890 operable to receive data from the size module 886 and the use module 888 to determine the optimal location within the device 802 to store the bottle. The space optimizer module 890 can randomly store the bottles based on frequency of use and size of the bottle. The space optimizer module 890 selects a particular location to manage the space within the device 802 and to efficiently store and retrieve a particular bottle when needed. The particular location for each bottle is stored in the database 832.

The stock module 885 also is operable to instruct the device 802 to obtain a weight of the bottle when positioned in the second port 846. The stock module 885 can access the NDC database 834 or other database to compare the measured weight to a predetermined weight established based on the read NDC barcode label on the bottle. If the measured weight is substantially similar to the predetermined weight, the stock module 884 can accept the bottle and instructs the carriage system 865 to retrieve the bottle from the second port 846 and position the bottle in a particular location determined by the optimizer program 885. If the measured weight is not substantially similar to the predetermined weight, the stock module 884 does not accept the bottle and transmits an instruction to the monitor 812 to request the pharmacy personnel to reconcile or explain the weight difference.

The software program 824 also includes a fill prescription module 892. The fill prescription module 892 is operable to receive data from the pharmacy management system 828 regarding a queue of prescriptions needing to be filled for a particular customer. The fill prescription module 892 also is operable to review the data in the queue to group various prescription entries together to prevent the customer from having to make several trips to the pharmacy. Pharmacy personnel select a prescription from the queue, and based on the selection, the fill prescription module 892 transmits instructions to the device 802 to obtain the bottle containing the medication needed to fill the selected prescription. The pharmacy personnel can select any prescription from the queue such that if a customer is waiting to pickup, the prescription can be filled just-in-time.

The fill prescription module 892 can communicate with the stock module 884 and/or the database 832 to obtain the particular location where the needed bottle of medication is stored within the device. The fill prescription module 892 can communicate the particular location of the bottle to the device 802 so the carriage system 865 knows where to go to retrieve the appropriate bottle. After the carriage system 865 retrieves the bottle, it places the bottle in the first port 842. The fill prescription module 892 instructs the scanner 826 to read the label on the bottle. The fill prescription module 892 compares the read data from the label with the selected prescription. If there is a match, the device 802 activates the door 850 to open so the pharmacy personnel can retrieve the bottle and count the appropriate number of pills to fill the prescription. If there is no match, the fill prescription module 892 instructs the device 802 to return the bottle to its shelf location.

The fill prescription module 892 also instructs the printer 816 to print a vial label to identify the medication and/or prescription being filled. When pharmacy personnel fill the customer vial with the medication, the label can be applied to identify the medication and the customer for whom the prescription was filled. When the customer picks up the filled prescription, pharmacy personnel can scan the vial label to print the customer information sheets.

Upon completion of the filling process, pharmacy personnel position the stock bottle in the second port 846. The fill prescription module 892 instructs the device 804 to scan the label on the bottle and obtain a weight of the bottle. The fill prescription module 892 compares the read data on the label and the weight to information in the NDC database 834 or other database to determine if the appropriate number of pills remains in the bottle after filling the prescription. If the read data on the label and the weight is substantially similar to the information in the NDC database 834 or other database, the fill prescription module 892 instructs the carriage system 865 to place the bottle on a shelf at its previous location or at a new location. Based on this instruction from the fill prescription module 892, the stock module 884 can activate the optimizer program 885 to find an appropriate location for the bottle. If the read data on the label and/or the weight is not substantially similar to the information in the NDC database 834, the fill prescription module 892 transmits an instruction to the monitor 812 for the pharmacy personnel to explain or reconcile the difference(s). If the particular medication is on a dangerous list (e.g., narcotics or addictive medications) and the pharmacy personnel need to explain or reconcile the difference, the fill prescription module 892 can require a pharmacist to verify the response. The response can be stored in the database 832. The fill prescription module 892 can then instruct the carriage system 865 to place the bottle on a shelf as noted above.

The software program 824 also includes an inventory check module 894. The inventory check module 894 is operable to maintain a current list of medications within the device 802. The inventory check module 894 also is operable to communicate with the database 832 to request inventory information stored therein. The inventory check module 894, when instructed, can provide a list of all medications within the device 802 and transmit the data to the printer 816 for a readable printout. The pharmacist can use the list to verify what is currently in the device 802. The list is accurate because pharmacy personnel expect the bottle to be the same when it comes out of the device and when it goes into the device 802, and the device 802 maintains a record of all prescriptions filled and thus, the remaining number of pills remaining in each bottle. The inventory check module 894 also allows the pharmacist to remove each bottle to check contents and return it to the device 802.

The software program 824 also includes a return to stock module 896. The return to stock module 896 is operable to transmit instructions to the device 802 to accept a customer vial of medication, which was not picked up from the pharmacy. The return to stock module 896 communicates with the stock module 882 to determine what medication is in the vial and a shelf location for the vial. The stock module 882 operates as discussed above to instruct the device 802 to receive and store the vial.

Figure 26:
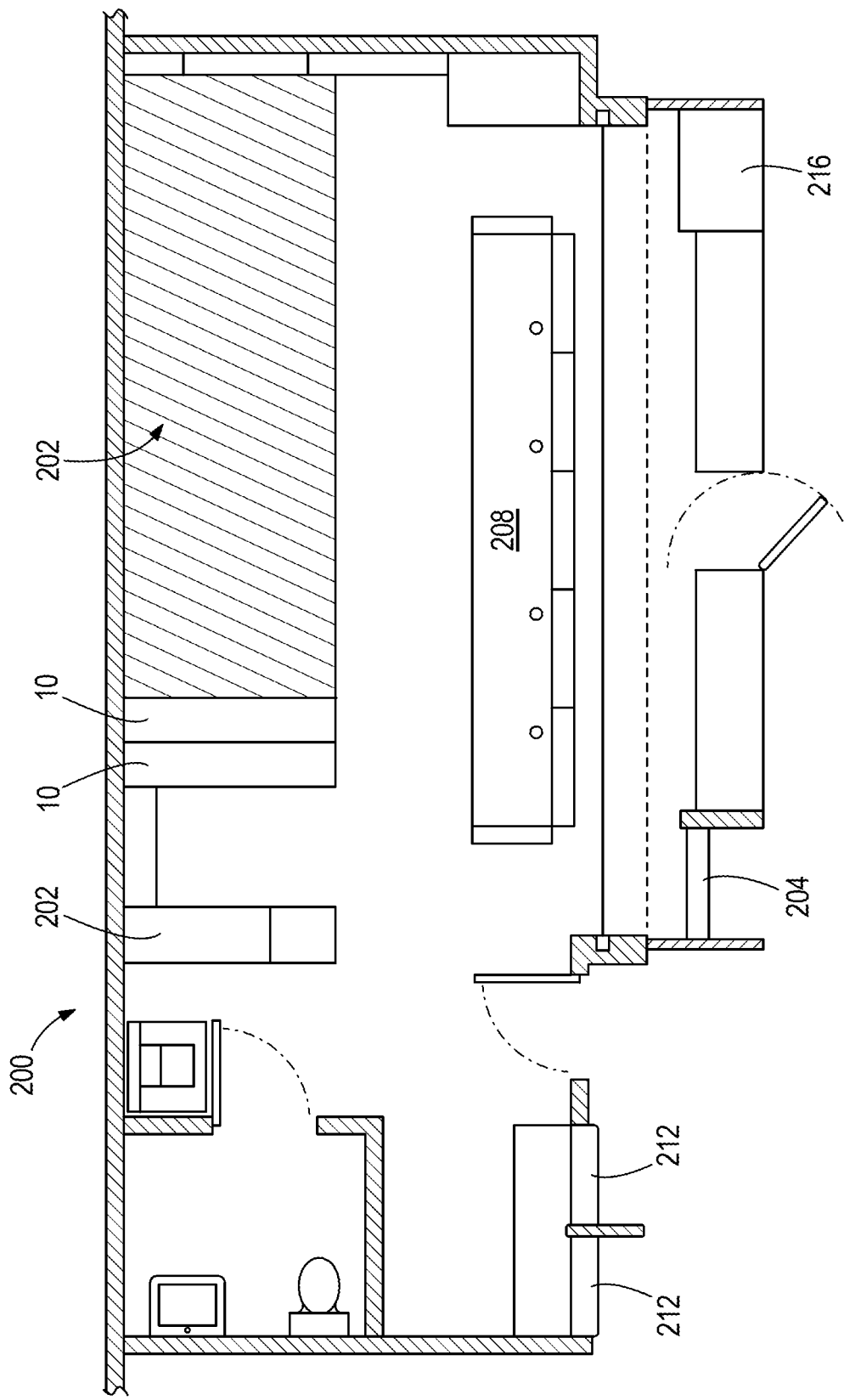
FIG. 26 is a layout of a floor plan of a pharmacy utilizing the pharmaceutical storage and retrieval device.

FIG. 26 illustrates one example of a floor plan of a pharmacy 200 using the pharmaceutical storage and retrieval device 10, 600, 802 in place of a traditional pharmacy shelving system 202. The pharmacy 200 includes drop-off windows 204 and a counter for a customer to drop off a prescription. The pharmacy 200 also includes a prescription filling counter 208, located to the interior of the floor plan, for a pharmacist or a technician to fill a prescription. The device 10, 600, 802, or in conventional layouts, the pharmacy shelving 202, is located to the rear of the pharmacy, with respect to customer drop off. Also toward the front of the pharmacy 200, adjacent the drop-off windows 204, are prescription pick-up windows 212 and a counter with at least one cash register. In some embodiments, as illustrated, the pharmacy 200 can include an Automatic Prescription Machine (APM) 216, as is known in the art.

Previously with conventional dispensing methods, once a customer drops off a prescription at window 204, a printer (not shown) near the drop-off window 204 prints a corresponding label. The printing process repeats for another prescription for another customer regardless of whether the prescription has been filled. The printed labels are generally very difficult to sort if there are a large amount of labels. Mistakes can be easily made in such cases.

Figure 27:
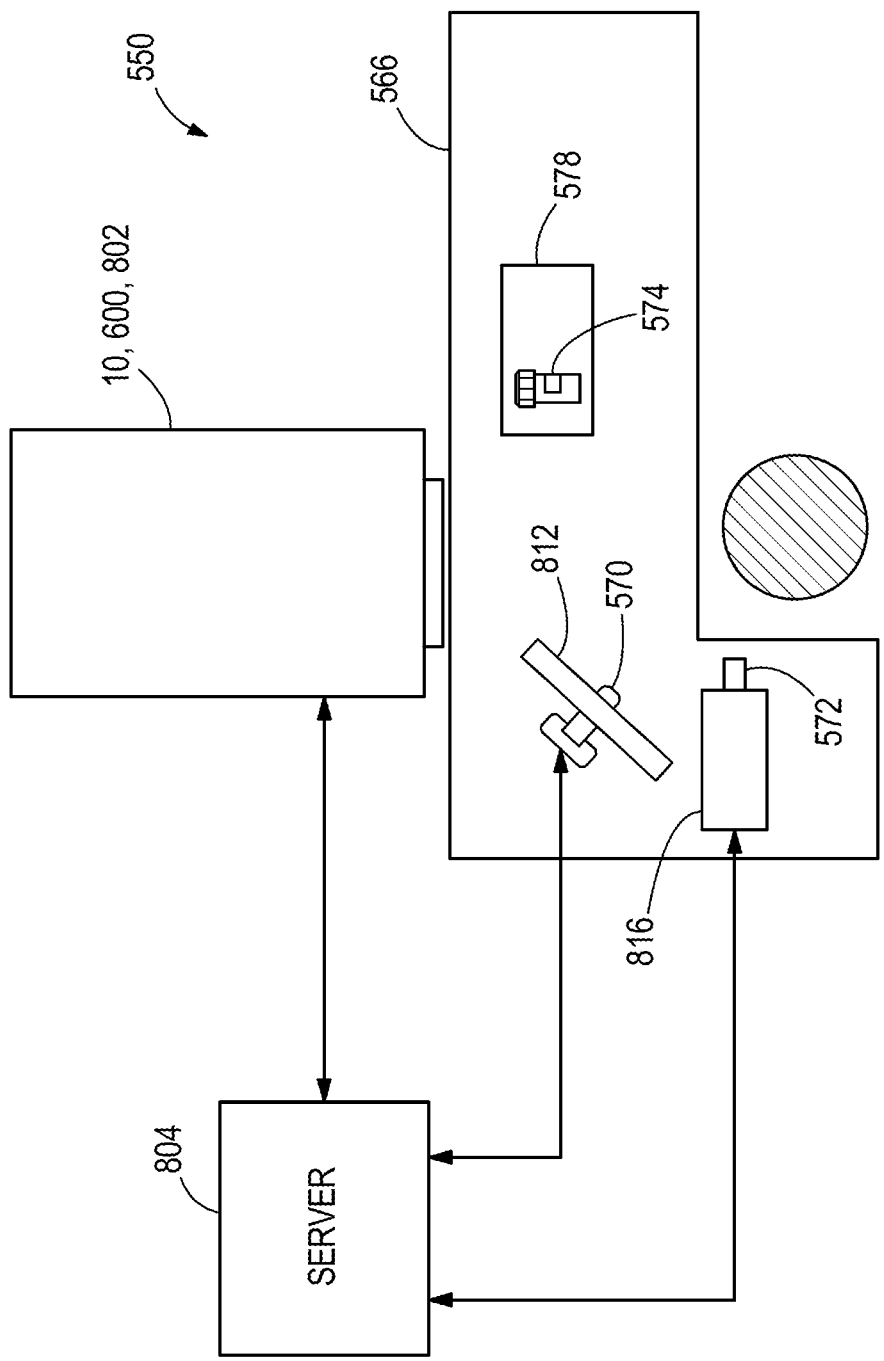
FIG. 27 illustrates a pharmacy personnel work cell for use with the pharmaceutical storage and retrieval device.

With the present invention, in one embodiment, the prescription information is entered into an electronic queue in the pharmacy management system 828, after the prescription has been dropped off at window 204. FIG. 27 illustrates a dedicated dispensing work cell 550 that includes a pharmaceutical storage and retrieval device 10, 600, 802, a monitor 812 and a printer 816 positioned on a counter 566. The dispensing work cell 550 or the device 10, 600, 802 may also be equipped with one or more imaging devices 570 such as a barcode scanner and/or a video camera. After a technician has successfully logged into the server 804 using, for example, the biometric device 820, the technician starts a prescription filling process as follows.

According to the queue in the PMS, the printer 816 prints a label 572 at a time only at the request of the technician stationed at the dispensing work cell 550. After the device 802 has retrieved the medication corresponding to the next prescription in the queue, the technician fills the prescription. Once the prescription has been filled in a vial 574 or while the device 802 is retrieving the bottle, the printer prints the appropriate label 572, and the technician adheres the label 572 onto the vial 574, and places the labeled vial 574 into a depository 578, such as, for example, a basket for a pharmacist to verify. The prescription filling process then repeats. Since the dispensing work cell 550 is for dispensing only, and the technician is provided with all things required to fill a prescription, filling prescriptions can be more efficiently performed by the technician.

In some embodiments, the imaging device 570 includes a video camera that is configured to image or record how a specific prescription is filled. For example, the video camera can record how a specific medication is counted when the prescription is filled to avoid or minimize any potential liability issues. For another example, the video camera can also capture who is filling the prescription for security reasons, and when the prescription is filled in real time. In some embodiments, the printed label 572 also includes a corresponding barcode. The barcode generally indicates various types of information related to the prescription and the customer. In such cases, imaging devices 570 such as a barcode scanner can also be configured to scan the printed barcode. In this way, the technician can ensure the information such as the prescription on the label corresponds to the information stored in the queue. Similarly, a time at which the barcode is scanned can also be recorded. For example, the time can indicate when the prescription is dropped off, filled, picked up, and the like. For example, after the prescription corresponding to the printed label has been filled, the technician can scan in the barcode to indicate that the prescription has filled at a specific time. For another example, when the prescription is picked up, a pick up time can be derived from a scan of the barcode at pick up. In this way, various types of information pertaining to the prescription and customer can be recorded for further analysis, if necessary.

Figure 28:
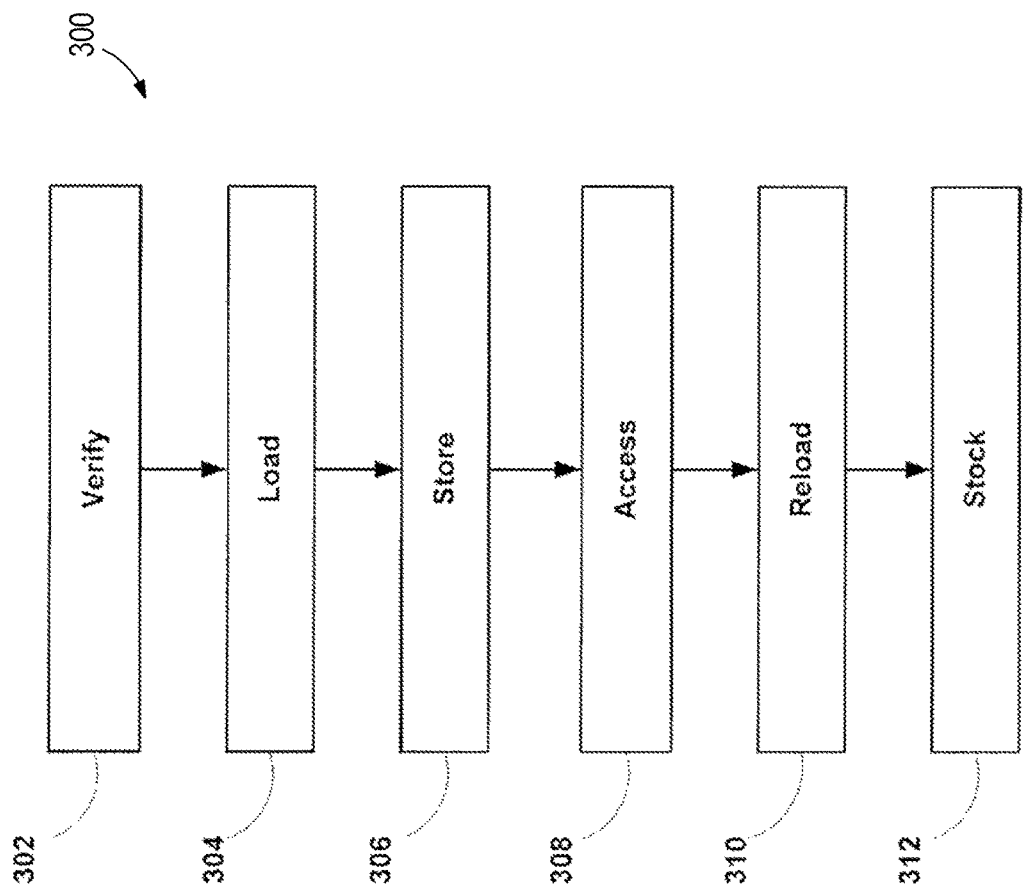
FIG. 28 is a flow chart of a method of operating a pharmaceutical inventory storage and monitoring machine according to some embodiments of the present invention.

FIGS. 28-35 illustrate flow diagrams of a method of operating the pharmaceutical storage and retrieval device 10, 600, 802 according to one embodiment of the present invention. As illustrated in FIG. 28, during operation 300 of the pharmaceutical storage and retrieval device 10, 600, 802, a user is verified to be an authorized user (at 302), an authorized user can load (at 304), securely store (at 306), access (at 308), reload (at 310), and stock (at 312) pharmaceutical inventory to and from the device 10, 600, 802. In a pharmacy 200, as shown in FIG. 26, a user of the device 10, 600, 802 is a pharmacist or a pharmacy technician. In order to load 304, access 308, or restock 312 inventory to or from the device 10, 600, 802, the user must first be identified (at 302) by inputting identification information to the access control device 60. For example, in some embodiments, the access control device 60 is a biometric sensing device 62, so the user would input identifying information such as their fingerprint, for example. The database 832 stores profiles of authorized users of the device 10, 600, 802. The server 804 compares the input from the user with the stored profiles in real time to check for user authorization. If user authorization 320 is verified at step 302, the user is enabled to proceed with loading 304, accessing 308, or restocking 312 the inventory in the device 10, 600, 802.

Figure 29:
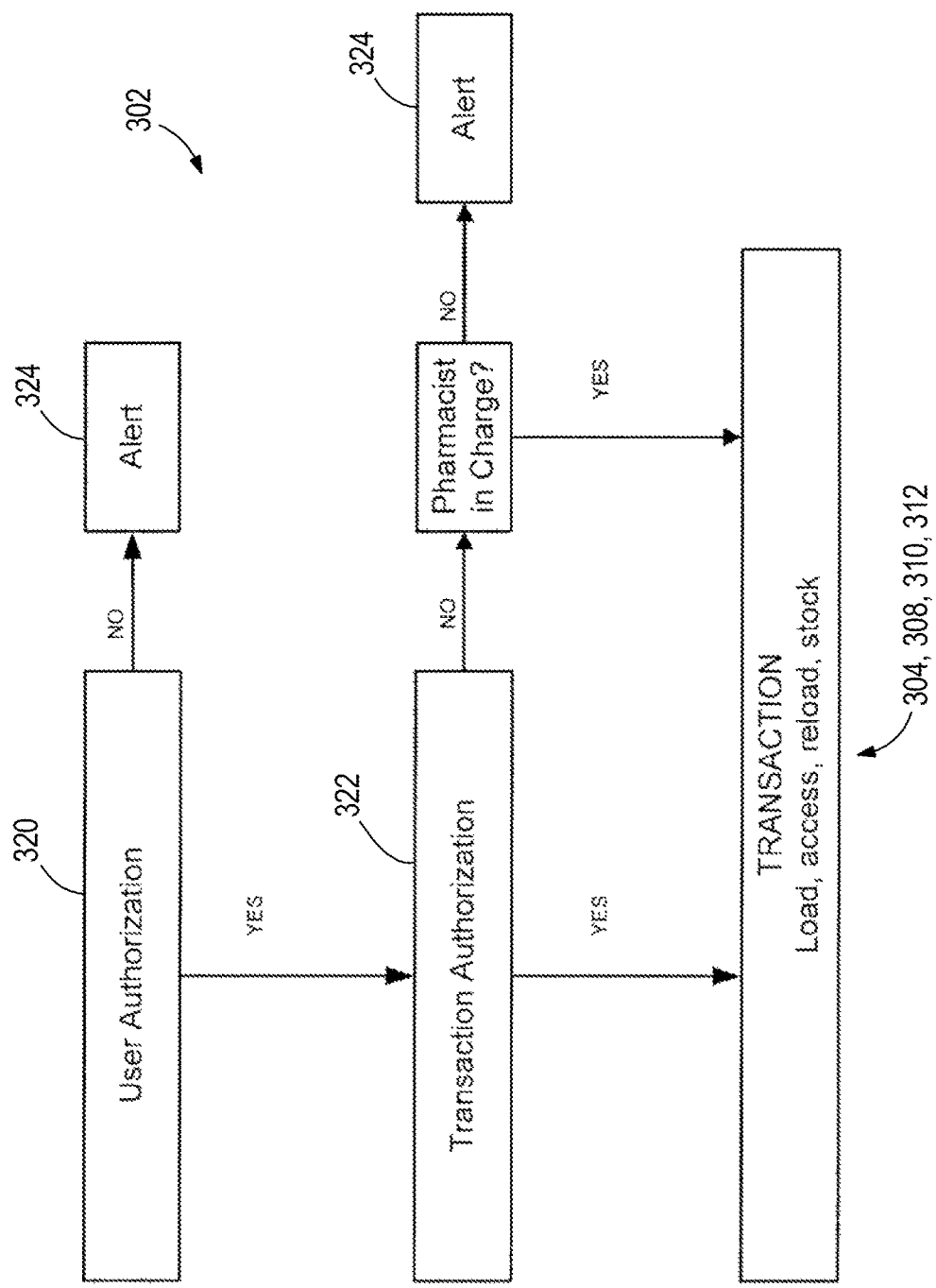
FIG. 29 is a flow chart of a part of the method of operating a pharmaceutical storage and retrieval device.

Based on the profiles, certain users may only have access to some of the inventory in the device 10, 600, 802. FIG. 29 illustrates a flow chart of the user authorization process 302. If user authorization is not verified at 320, or the user is authorized, but is not performing an authorized transaction 322, the user will not be granted use of the device 10, 600, 802 or access to the inventory stored within the device 10,

600, 802, and in some embodiments, the server 804 may signal an alert 324. However, a pharmacy manager or pharmacist in charge can have an override code to gain access to the device 10, 600, 802 under any conditions, even if there is not a prescription order to fill.

Typically, a high percentage, such as, for example, 25 percent, of all prescriptions are not picked up after the prescriptions have been submitted and filled. In such cases, some items may be considered temporarily out of stock, and require substantial amount of time and money to restock. With embodiments of the present invention, once the user has been authorized to access the device 10, 600, 802, the user or the pharmacist can use the software program 824 to fill a prescription with the device 10, 600, 802 for a customer when the customer shows up at the pharmacy, or when the prescription is about to be picked up. In this way, efficiency is increased, and cycle time can be reduced from about a typical benchmark such as three to five minutes to about 15 to 30 seconds.

Previously, with existing dispensing methods and apparatus, it takes about a day to stock any new medication. It is generally a time consuming and labor intensive task. For example, manual (re)stocking requires cross-referencing an order list. After cross-referencing the order list, an exception report is generated to indicate whether an ordered medication is in stock or is missing.

With the present invention, and particularly with the traveler 140, the robotic arm 144, the server 804, the device 10, 600, 802 can store the new stock of medication in any suitable order. Specifically, when a medication is stocked initially with the traveler 140 or gantry system 838, the server 804 can be configured to remember and retrieve where the particular medication has been stored and when a shelf is available. In other words, while the device 10, 600, 802 can store medications in any order, such as, for example, an alphabetical order, the device 10, 600, 802 does not require the new stock to be stored in the same order. In this way, (re)stocking can be performed at a faster rate, hence improving efficiency, and an exception report can be generated immediately. In some instances, the time required to store or stock a medication is about ten to fifteen seconds.

Figure 30:
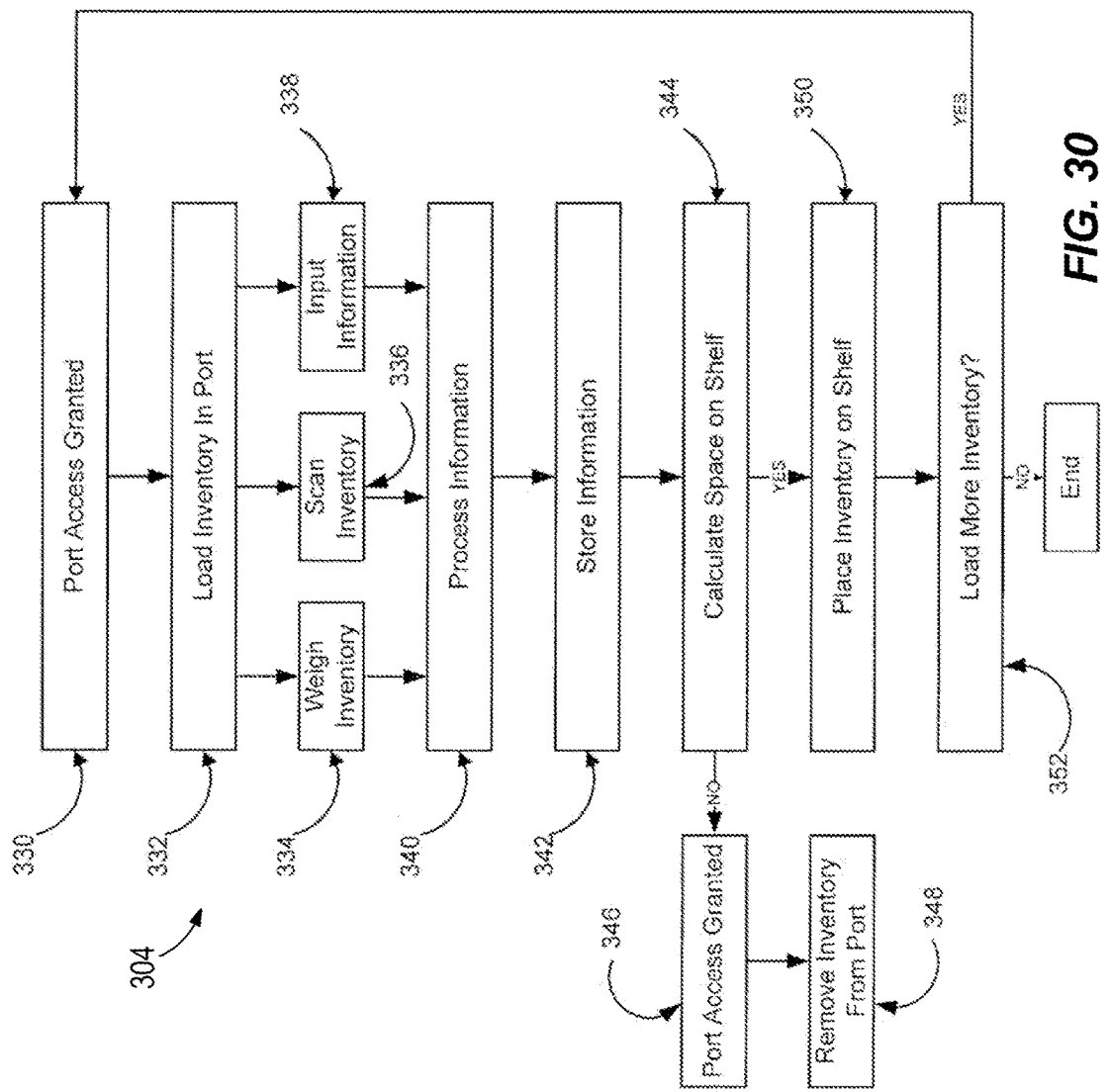
FIG. 30 is a flow chart of another part of the method of operating a pharmaceutical storage and retrieval device.

FIG. 30 illustrates a loading process 304 of the pharmaceutical storage and retrieval device 10, 600, 802. The user must first obtain access to the machine through the identification verification process 302, as described above and illustrated in FIG. 29, to load the pharmaceutical storage and retrieval device 10, 600, 802 with inventory items. The user must then confirm on the monitor 812 that they are loading inventory into the device 10, 600, 802, and in some cases, confirm the inventory items that they are loading 304. When the user is identified and authorized and the loading activity is verified, the access door 624 (850) to port 604 (846) opens (at 330) and the user may proceed with loading one or more inventory items into the device 10, 600, 802.

The inventory items are typically loaded into the device 10, 600, 802 while remaining in its native packaging, as provided by the manufacturer. In its native packaging, pharmaceutical inventory is typically in the form of bottles of prescription medication, in tubes of prescription medication, flat packs, or the like. Inventory in which the native packaging is not a bottle, or similarly manageable container, can be placed into a container (e.g., clear cup) or holder to be loaded into the device 10, 600, 802. With the inventory item is still in its native packaging, the user places the inventory into the port 604 (846) (at 332). When the inventory item is in the port 604 (846), the port access door 624 (850) will close, and the inventory will be weighed (at 334) and scanned (at 336). While in the port 604 (846), the inventory item sits on top of the scale 622 (882) or on top of the platform 612 (880) and is moved to the scale 622 (882). The scale 622 (882) measures the weight of the inventory and stores the value using the server 804. The scale 622 (882), the platform 612 (880), or the arm 144 (872) rotates to move the inventory item into the desired orientation to provide access to the scanner 626 (881) or the bottle is positioned in such a way that the scanner 626 (881) can read the information on the label. The scanner 626 (881) scans the inventory item and sends the information received to the server 804. In some embodiments, the scanner 626 (881) reads the barcode on the native packaging of the inventory. In alternate embodiments, the scanner 626 (881) can also image the packaging of the inventory through a profile contrast technique to determine information such as the size and shape of the inventory or read information from the packaging label, such as expiration date or Lot number. In still alternate embodiments, the scanner 626 (881) can be a multifunction visual system. The visual system scanner 626 (881) can image the inventory physically to determine the size (diameter, height, etc.) and shape of the bottle. This allows the server 804 to make calculations regarding available space so as to minimize open space on the shelves 102 (876) with respect to both width and height when choosing a location for the bottle. The visual system scanner 626 (881) can also record a visual image of the inventory labels and using cognitive capacity software, the system can read the characters on the labels. The server 804 and/or database 832 stores the visual images of the labels for pharmacy records (which can be in the form of a PDF or the like) and extracts, analyzes, and stores the information read from the labels, such as the type of medication, the strength of medication, and the amount of medication in the bottle (i.e., number of tablets, volume of liquid, etc.) or reads the National Drug Code (NDC) and determines information from a table or directory.

In some embodiments, the user can utilize the monitor 812 to input additional information (at 338) regarding the inventory item into the server 804, including the type, size, expiration date, Lot number, etc. In some embodiments, the server 804 processes (at 340) the information and can use algorithms to calculate additional information pertaining to the inventory. The server 804 can use the algorithms to calculate the weight of the inventory packaging. For example, from the barcode or label image, the server 804 can use the number of medication tablets or data table provided by drug manufacturers multiplied by the weight (usually in milligrams) of each tablet to determine the weight of the actual medication inventory within the inventory packaging. The weight of the actual medication within the packaging is subtracted from the total weight as measured by the scale 622 (882) to determine the weight of the inventory packaging. The server 804 and/or database 832 saves (at 342) this information along with the rest of the information extracted from the outputs of the scale 622 (882) and scanner 626 (881).

The information acquired by the device 10, 600, 802 through the scale 622 (881), the scanner 626 (881), the monitor 812, and the algorithms is processed by the server 804 and stored (at 342) in the database 832. The server 804 compares the type of inventory with an internal database for medications, usually determined from the NDC directory. If the type of inventory item sitting in the port 604 (846) is not included in the internal database, for example, if the inventory were not a medication, the device 10, 600, 802 can show an alert on the monitor 812 for the user to remove the inventory item from the port 604 (846). The server 804 also can access previous entries of inventory to determine the locations and sizes of space available (at 344) on the shelving system 100 in the device 10, 600, 802. If the size of the inventory item is greater than the size of unused space at any location on the shelving system 100, the device 10, 600, 802 can display an alert on the monitor 812 and the port access door 624 (850) opens (at 346) for the user to remove (at 348) the inventory item from the port 604 (846). If the size of the inventory item is less than or equal to the size of unused space on the shelving system 100 (875), the machine 10, 600, 802 can remove the inventory item from the port 604 (846) and move it into the interior of the housing 12 using the carrying device 142 (872). The server 804 determines which carrying device 142 (872) to use to move the inventory based on the information stored in the database 832 regarding weight calculation from the scale 622 (882) and the size and shape information from the scanner 626 (881). The transfer mechanism 140 moves the robotic arm 144 toward the port 604 (846) until the carrying device 142 (872) reaches a point where the inventory item is within reach. The carrying device 142 (872) picks up the inventory item and the transfer mechanism 140 moves the robotic arm 144 toward the predetermined, most appropriate, available space on one of the shelves 102 on which to place (at 350) the inventory item.

In some embodiments, the device 10, 600, 802 stocks the shelves 102 (876) nearest the port 604 (846) first, and continues to load the inventory moving farther away from the port 604 (846). In alternate embodiments, the placement on the shelving system 100 (875) for each type of inventory is preset based on size, weight, and frequency of use. However, the placement on the shelving system 100 of the inventory can be changed by users who are authorized to do so. Alternatively, the device 10, 600, 802 also can be programmed to continually reorganize the placement of the inventory on the shelving system 100 (875) based on the calculation of algorithms by the server 804 to maximize the efficiency of the device 10, 600, 802 according to frequency of inventory use and size of inventory packaging. For example, inventory that is used more often would be placed closer to the port 604 (846) so as to minimize work of the transfer mechanism 140 by minimizing the movement distance of the robotic arm 144, and therefore minimizing time to retrieve the inventory from the shelf 102 (876). Additionally, the device 10, 600, 802 accounts for the size and weight of the inventory, so that there are as few open spaces as possible between packages of inventory on the shelves 102 (876) and in the vertical distance between shelves 122. Once the inventory is placed in its designated location on the shelf 102, the server 804 links the information regarding the placement of the inventory with the information regarding the type, size, and weight of the inventory. The user can then load another piece of inventory (at 352) into the device 10, 600, 802 if there remains additional inventory to load.

In other constructions of the device 10, 600, 802 having more than one port 604, the user can load inventory using all of the ports 604 at the same time. Alternatively, the user can load the device through the loading port. Multiple packages of inventory can be placed onto the angled ramp to be automatically fed into the loading port. The loading scale and loading scanner are connected to the server 804 and function as the scale 622 and scanner 626, respectively, during loading, as described above.

Figure 31:
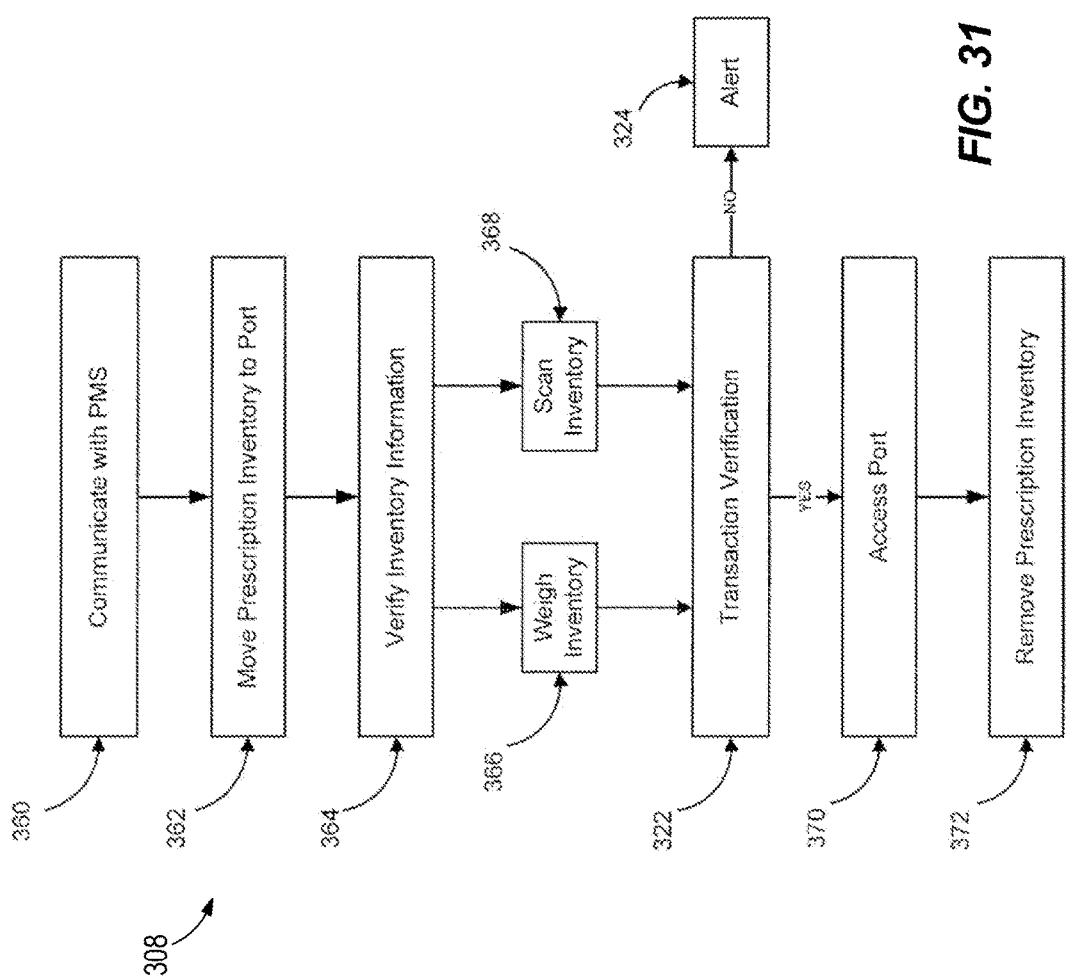
FIG. 31 is a flow chart of still another part of the method of operating a pharmaceutical storage and retrieval device.

To access and remove the inventory from within the pharmaceutical storage and retrieval device 10, 600, 802, the user must first obtain access to the device 10, 600, 802 through the identification verification process 302, as illustrated in FIG. 29. When the user is identified and verified as an authorized user, they may proceed with accessing and removing inventory from the device 10, 600, 802, as illustrated in FIG. 31. The user informs the device 10, 600, 802 of the type of inventory that they wish to remove by inputting the information to the server 804 using the monitor 812. The server 804 accesses the database 832 to determine the location on the shelving system 100 of the desired inventory. The transfer mechanism 140 moves the robotic arm 144 and the carrying device 142 to the location on the shelving system 100 (875) of the desired inventory. The carrying device 142 picks up the piece of inventory, and the transfer mechanism 140 moves the robotic arm 144, the carrying device 142, and the inventory to the port 608. When the inventory is aligned with the port 608, the carrying device 142 releases the piece of inventory onto the scale 622 of the port 608. In some embodiments, the scale 622 confirms the weight of the inventory with the value stored on input of the inventory, and the scanner 626 confirms the barcode and/or image and profile of the inventory item with the information stored on input of the inventory. When all information is confirmed, the port interface door 624 opens to allow the user to remove the inventory item from the port 608. In embodiments of the device 10, 600, 802 having more than one port 608, the device 10, 600, 802 can remove more than one piece of inventory at one time, or use a one-in-one-out system. The device 10, 600, 802 with multiple ports 608 can include colored lights that illuminate to indicate that the inventory in a given port 608 is for a particular user that has been assigned to that color.

In some embodiments, the server 804 can be programmed to only allow access to the inventory in the device 10, 600, 802 when the device 10, 600, 802 is connected with the network 808 and it is indicated that a particular medication is needed to fill an order. The server 804 communicates (at 360) with the pharmacy management system 828 and software through the network 808 to inform the device 10, 600, 802 of prescriptions that are being processed. When a pharmacist enters a prescription into the pharmacy management system 828, the server 804 communicates (at 360) with the pharmacy management system to access the prescription information. The server 804 recalls the location of the medication for the prescription being processed and instructs the transfer mechanism 140 to move to the location on the shelving system 100 proximate to the needed medication and removes that medication from the shelf 102 using the carrying device 142. The transfer mechanism 140 transports (at 362) the medication to the port 608 where it waits for a user to access the device 10, 600, 802 to fill the prescription.

In some embodiments, the device 10, 600, 802 verifies the inventory information (at 364) while the inventory is in the port 608, such as reweighing (at 366) and rescanning (at 368) the inventory to determine whether the device 10, 600, 802 obtained the correct medication or an incorrect medication. When the user is identified and verified, the medication for the prescription is already located near the port 608. To access the medication inventory, the user selects a prescription from the queue to fill next. When the user is identified and has selected the prescription to fill, the port access door 624 opens (at 370) to allow the user to access the medication (at 372). If the user is the pharmacist in charge, that user can use an override code to access the device 10, 600, 802 without a valid order being processed. If the device 10, 600, 802 has more than one port 608, multiple prescriptions can be filled at once using colored lights that illuminate to indicate that the inventory in a given port 608 is for a particular user that has been assigned to that color.

In some embodiments, the device 10, 600, 802 will not enable the port interface door 624 to open for inventory removal from the port 608 until the amount of inventory for use has been confirmed. The server 804 communicates with the pharmacy management system 828 to determine how much of the inventory from a container actually needs to be removed for use.

Figure 32:
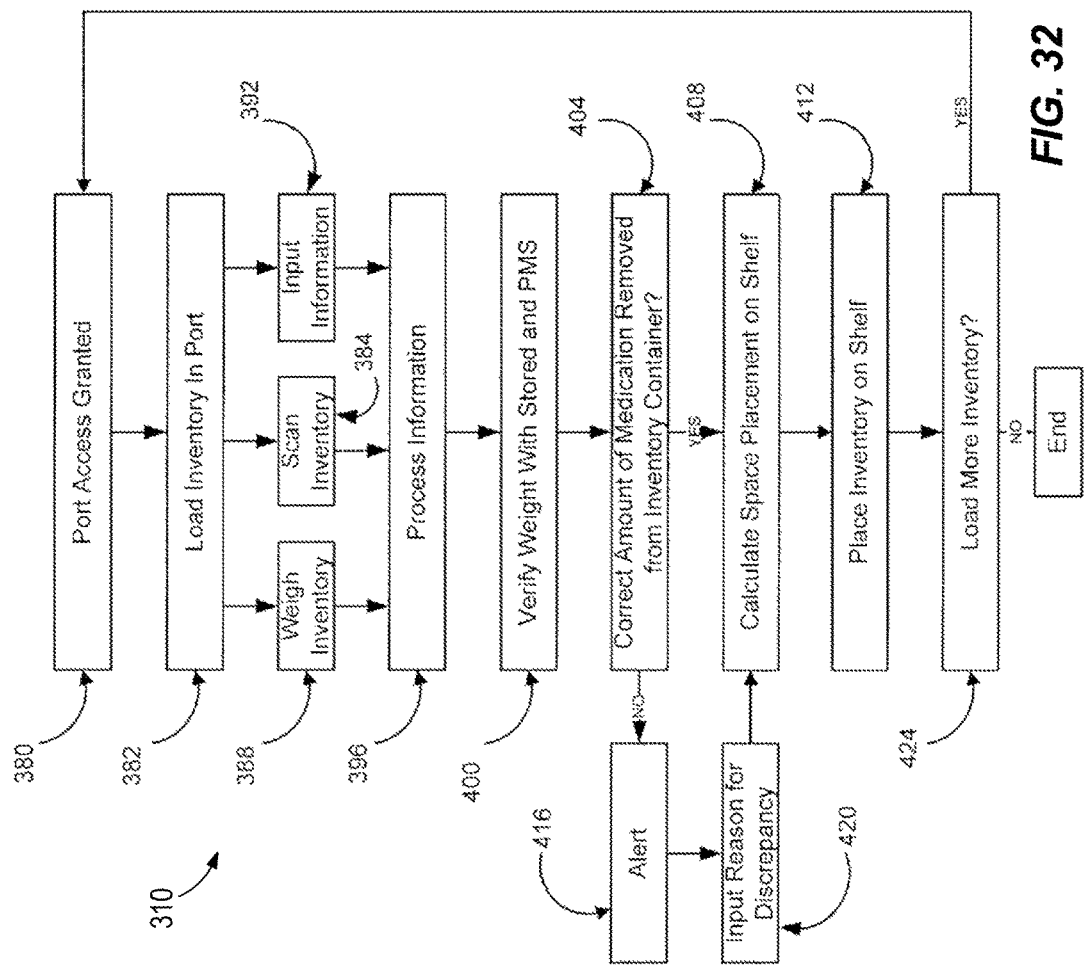
FIG. 32 is a flow chart of an additional part of the method of operating a pharmaceutical storage and retrieval device.

FIG. 32 illustrates a flow chart of returning inventory previously removed from within the pharmaceutical storage and retrieval device 10, 600, 802, i.e., a restocking process 310. The user first obtains access to the device through the identification verification process 302. When the user is identified and authorized, and their intended activity is verified, access to port 604 is granted (at 380) and the user may proceed with returning the inventory to the device 10, 600, 802. Since the medication had previously been removed from the device 10, 600, 802 to fill a prescription for a number of tablets of that medication, the information regarding the inventory is already stored in the server 804. The user positions the medication inventory bottle back into the port 604 (at 382) to return the unused medication to the device 10, 600, 802 for storage. The scanner scans (at 384) and scale 622 weighs (at 388) the bottle of medication and uses the server 804 to verify that the correct amount of medication was withdrawn from the bottle. In some constructions, the user can utilize the monitor 812 to input additional information (at 392) regarding the inventory item into the server 804. Based on the stored weight of the bottle, calculated upon initial loading and verified upon each loading thereafter, and the number of tablets that should have been removed for the prescription, as determined by the input of the user upon removal of the medication from the device 10, 600, 802 and verified by the input received from the pharmacy management system 828, the server 804 processes (at 396) the information and may use algorithms to determine what the new weight of the bottle and remaining inventory should be. The new weight of the bottle is compared (at 400) with the measured weight of the bottle. If the new weight value is the same as the measured weight based on the information input to the server 804, the inventory item can be reloaded into the device 10, 600, 802. The server 804 determines the locations and sizes of space available (at 408) on the shelving system 100 in the device. The shelving system 100 removes the inventory from the port 604 and moves (at 412) it to an appropriate shelf 102. If the new weight value is not the same as the measured weight based on the information input to the server 804, the server 804 can generate and the monitor 812 can display (at 416) an alert requesting the user to recount the number of pills in the bottle or prompting the user to input (at 420) a reason why the new weight does not match the measured weight, such as, for example, "Return (a number) of Pills" for a filled prescription that has more than the prescribed amount, "Add (a number) of Pills" for a filled prescription that has less than the prescribed amount, or "Three pills were dropped while filling the prescription." Depending on the value of the discrepancy, the type of medication, and the authorization of the user, the user may need to get the pharmacist in charge to verify the reason for discrepancy in weight. The server 804 can record the discrepancy on the profile of the user, and in some cases, a report may be sent to the pharmacist in charge. The process can continue (at 424) as described above for additional inventory items.

Once the discrepancy has been recorded or if the difference between the stored values and current values is the same as the amount that had been communicated to the device 10, 600, 802 from the pharmacy management system 828, the inventory can be reloaded into the device 10, 600, 802 as described above during the loading process 302. Some inventory can be returned to the same or different location on the shelving system 100 during reloading that it had been placed in during loading. However, the server 804 can continuously process algorithms relating to frequency in use of inventory, size and weight of inventory, and available space on shelves 102. Based on these calculations, the reloaded inventory can be placed in a different location on the shelving system 100 than it had been located before removal.

Figure 33:
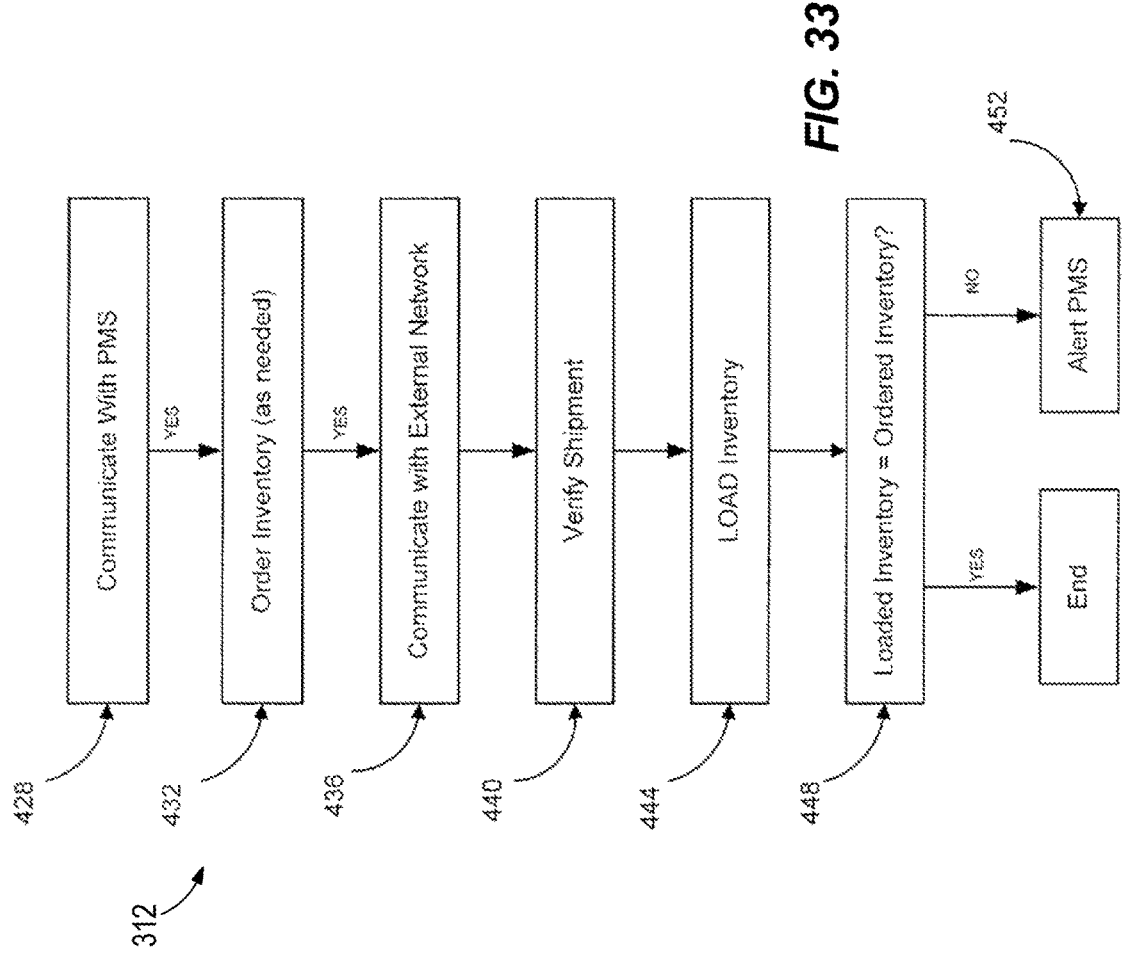
FIG. 33 is a flow chart of another additional part of the method of operating a pharmaceutical storage and retrieval device.

FIG. 33 is a flow chart that illustrates a stocking process 312 of the pharmaceutical storage and retrieval device 10, 600, 802. Based on calculations relating to frequency in use of inventory, size and weight of inventory, and information received from the pharmacy management system 828, the server 804 can make calculations to predict when the inventory will be used up and when to order more. The server 804 can communicate (at 428) this information to the pharmacy management system 828 or the monitor 812 to alert a user or set of users that a particular medication needs to be reordered (at 432). When a particular medication inventory is out of stock, that information can also be communicated to the pharmacy management system 828 though the network 808 or over the monitor 812 to a user or set of users. In some embodiments, the device 10, 600, 802 can send alerts after a set amount of time regarding which inventory items are out of stock and/or which inventory items will likely be out of stock within another set time period. Further, the device 10, 600, 802 can warn the user when there may be inadequate inventory to fully fill an order.

In some embodiments, the server 804 can communicate (at 436) over the network 808 with the manufacturers or distributors of the inventory located inside the device 10, 600, 802. Depending on the information from the manufacturers, the device 10 can perform certain actions or send alerts to the pharmacy management system 828 or to a user or set of users. When an order of inventory is sent from a manufacturer or distributor, the server 804 communicates with the network 808 regarding the expected shipment of inventory 390. The device 10, 600, 802 stores and verifies (at 440) the information for the pharmaceutical inventory that is expected to arrive with that shipment and be loaded into the device 10, 600, 802. When the delivery of medications arrives, the inventory items are loaded (at 444) such that the loading process is expedited because the device 10, 600, 802 has a record of the inventory that should be loaded. The device 10, 600, 802 can verify (at 448) the shipment of inventory items by comparing the medication inventory that was loaded with the stored record of the medication inventory that was expected to be loaded. If there were any errors in shipping or delivery, the server 804 can send (at 452) an alert to the monitor 812, the pharmacy management system 828 and/or the network 808. Therefore, the pharmacists, manufacturers, and distributors can quickly pick up on errors and correct them, as needed. Further, if a manufacturer or distributor issues a recall on certain products, they can communication the recall information essentially instantaneously to the server 804. The server 804 can block access to the recalled inventory and alert the users, through the monitor 812, not to use the products that were recalled.

Under certain operating conditions, the pharmaceutical storage and retrieval device 10, 600, 802 operation can be overridden. The pharmacist-in-charge can override the device 10, 600, 802 under any conditions by using the key or their personal code. Conditions under which the device 10 can be overridden include, for example, a power outage, server 804 failure, or the like. When the device 10, 600, 802 is overridden, the device 10, 600, 802 can be unlocked by a key, a code, or the like, and opened so that the inventory therein can be accessed. In some embodiments, one or both of the sides 18, 20 of the housing 12 can be unlocked and can swing open for access to the interior of the housing 12. In other embodiments, the front 14 can be unlocked and pulled forward with the shelving system 100 out of the housing 12, exposing the inventory on the shelves 102 for access. In still alternate embodiments, another override system can be used to access the inventory within the housing 12. When the device 10, 600, 802 is returned to operation, the sides 18, 20 and/or the front 14 should be closed and relocked and all of the inventory must be checked for tampering, either manually or automatically, and should be reloaded and reweighed. The post-override weight is compared to the pre-override weight. Any differences in inventory weight should be accounted for before continuing with further operation of the device 10, 600, 802.

The pharmaceutical storage and retrieval device 10, 600, 802 can be used in pharmacies 200 in place of the traditional pharmacy shelving 202. When medication inventory is shipped to the pharmacy 200, the pharmacist can load the inventory, still in its native packaging, directly into the device 10, 600, 802. The device 10, 600, 802 records the inventory that was loaded, so the pharmacist will be informed soon after delivery if a particular piece of inventory is missing.

The pharmaceutical storage and retrieval device 10, 600, 802 can be used daily in any pharmacy 200 in place of the traditional pharmacy shelving 202. A customer can drop off a prescription with a pharmacist, a technician, or a clerk at the drop off windows 204 of the drop off counter 206. Using the pharmacy management system 828, the pharmacist performs a Drug Utilization Report (DUR) and obtains insurance and pricing reports. If the DUR is satisfactory, the pharmacist enters the customer information into the PMS. The pharmacy management system 828 communicates with the server 804 so that the server 804 receives the prescription information. The device 10, 600, 802 can have the particular medication for the prescription ready in the port 608, so that the pharmacist or technician only has to verify their identification information to access the medication for that prescription. The pharmacist or technician fills the prescription as described above. If the device 10, 600, 802 determines that stock of a particular medication is low at any time, it can communicate with the pharmacy management system 828 to alert the pharmacist to order more. The filled prescription is placed into a prescription holding or into an APM 216 for customer pickup. Before giving the prescription to the customer or placing it in the APM 216, the pharmacist uncaps the filled prescription and checks the type and amount of medication with the pharmacy management system 828 to prevent errors. The customer can pick up their prescription either at the prescription pick-up window 212 from the pharmacist or at the APM 216.

In other embodiments, the server 804 automatically schedules a return day of an unused medication for a refund. For example, after the device 10, 600, 802 has weighed a stock bottle with the scale 622, and scanned in information on the stock bottle, the scanned information such as lot numbers and expiration dates are extracted and recorded. As an expiration day approaches, for example, within a predetermined amount of time prior to the expiration day, the server 804 generates an alert to the pharmacy or user of the approaching expiration day. In this way, the pharmacy can determine to return any unused portions of a medication whose expiration day reaches the predetermined amount of time.

Similarly, the server 804 also selectively automatically generates a medication consumption rate. For example, after the device 10, 600, 802 has received a stock bottle at the port 846, the scale weighs the stock bottle and records the initial weight. When the stock bottle is checked out, after an amount of medication is taken out of the stock bottle, and stock bottle is checked back in, the stock bottle is again weighed on scale and returned to a location on the shelf 102. The server 804 compares the check-out weight with the check-in weight to obtain a weight differential. The server 804 then determines a rate of consumption based on the weight differential and other factors, such as, for example, an amount of time since the stock bottle or the medication is initially stocked.

Different orientations of the stock bottles can reduce the overall size of the device 10, 600, 802, and/or increase the capacity of the device 10, 600, 802. For example, bottle height varies from about two to about 12 inches, whereas bottle diameter varies from about one to about four inches. Therefore, bottle height ratio varies from one to five times, bottle diameter ratios varies from one to two times. Therefore, if stock bottles are stored on their sides, the capacity of the inventory machine can be increased. For example, when the device 10, 600, 802 has dimensions of about 20 inches by about 78 inches by about 78 inches, the device 10, 600, 802 has a capacity of about 1,500 bottles of various sizes. To ensure that the bottles do not slide from side to side, rubber gaskets are used to pad the shelves into which bottles are inserted. In such a case, the carrying device 142 can be configured to grab the cap of a bottle rather than its sides. Additionally, holding the bottle at its cap allows imaging devices to read information on the bottle, if desired.

Figure 34:
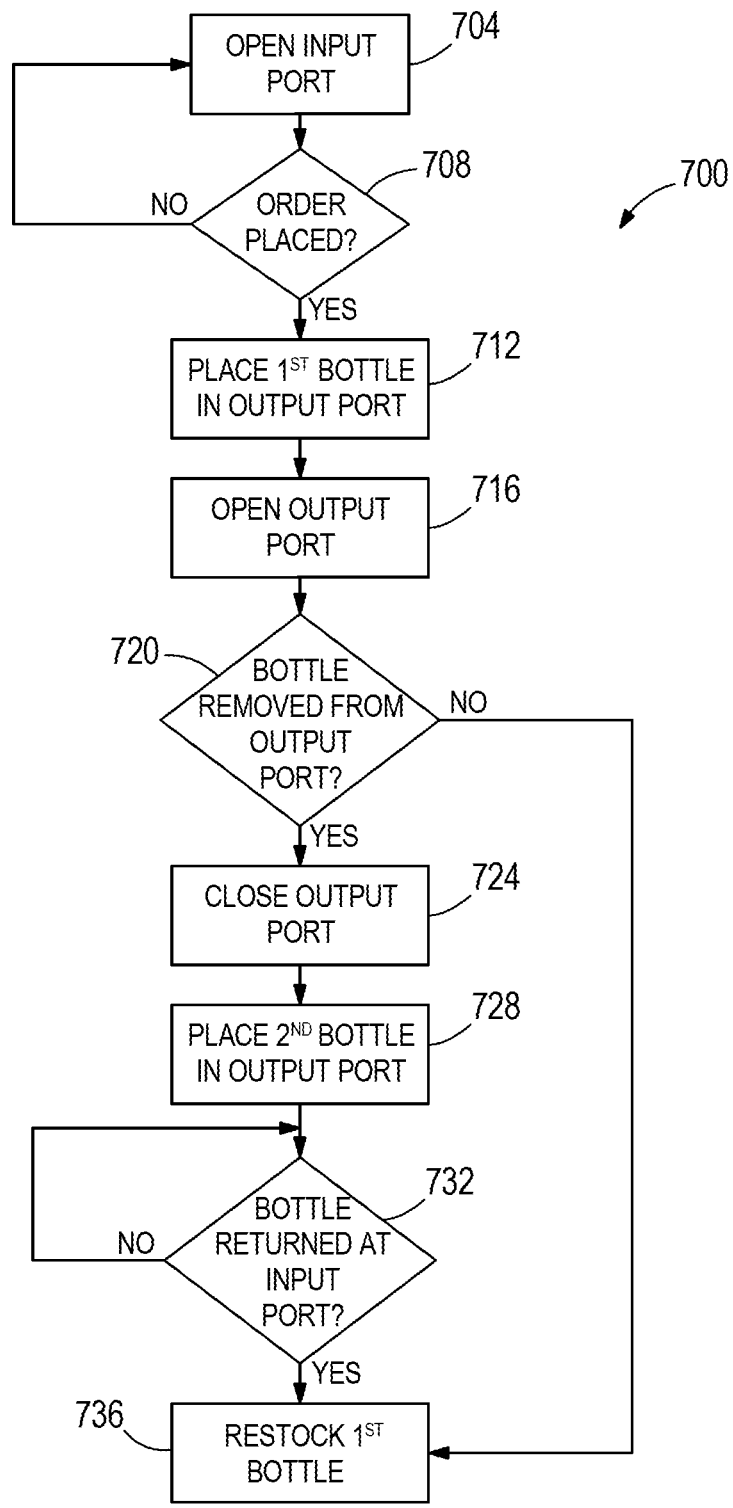
FIG. 34 is a flow chart of an exemplary dispensing operation of a pharmaceutical storage and retrieval device.

In an exemplary dispensing operation 700 (assuming the front and back doors 624, 628 move in opposite direction simultaneously), as shown in FIG. 34, the device 600, 802 through the server 804 opens (at 704) the output port 608 at the back plane 631 (while the input port 604 is closed and the output port 608 is closed at the front plane 630). After an order has been placed (at 708), the robotic arm 144 places a stock bottle (at 712) according to the prescription onto the platform 616. The output port 608 is then opened (at 716), while the input port 604 is closed. After the bottle has been removed (at 720) from the output port 608, the output port 608 is closed (at 724) while the input port 604 is open. In this way, the robotic arm 144 can place (at 728) another bottle (according the queue in the computer) on the platform 616 in the output port 608. While the input port 604 is open, the device 600, 802 waits for the user to replace (at 732) the first bottle back onto the platform 612 to be restocked (at 736). The dispensing operation is repeated then at 716.

In order to increase its capacity, the device 600 also includes a plurality of shelves 640 as illustrated in FIG. 5. Specifically, the shelves 640 of the device 600 are above and below the port 604, and directly accessible by the robotic arm 144. Similarly, the shelves 640 of the device 600 are above the output port 608 and below the input port 604, and directly accessible by the robotic arm 144. In some embodiments, the shelves 640 are about 12 inches deep for storing oversized objects. Each of the shelves is also shown to include supporting pads 644 such as rubber gaskets to protect bottles therein.

The embodiments described above and illustrated in the figures are presented by way of example only and are not intended as a limitation upon the concepts and principles of the present invention.

What is claimed is:

1. A method of stocking a pharmaceutical storage and retrieval device, the pharmaceutical storage and retrieval device including a housing, a port supported by the housing, a first door movably coupled to an exterior of the housing to selectively cover the port, a scanner supported by the housing within the port, a second door movably coupled to an interior of the housing to selectively cover the port, a scale supported by the housing within the port, and a gantry system positioned within the housing, the gantry system including a gripper assembly and a motor coupled to the gripper assembly to move the gripper assembly within the housing, the method comprising:

inputting identification information of a user into the pharmaceutical storage and retrieval device;

verifying the identification information of the user of the pharmaceutical storage and retrieval device;

opening the first door to the port of the device, the port being accessible from outside of the pharmaceutical storage and retrieval device, wherein the port is defined between the first door and the second door of the pharmaceutical storage and retrieval device;

positioning an inventory item in the port between the first door and the second door and closing the first door;

weighing the inventory item while the inventory item is in the port using the scale of the device to determine a weight value of the inventory item;

storing the weight value of the inventory item in a database;

reading a label on the inventory item while the inventory item is in the port using the scanner of the device to identify a medication type;

determining whether the medication type is included in the National Drug Code database;

when the medication type is not included in the National Drug Code database:
  generating an alert on a user interface of the pharmaceutical storage and retrieval device,
  opening the first door to the port of the device, and removing the inventory item from the port;

determining a size of unused space in the pharmaceutical storage and retrieval device;

determining a size of the inventory item;

storing the medication type in the database;

determining, by a processor coupled to the database, an amount of medication within the inventory item based on the weight value from the scale and the medication type from the scanner;

storing a value indicative of the amount of medication within the inventory item in the database;

comparing the weight value with an expected weight;

wherein when the weight value is substantially similar to the expected weight, identifying an available space in the pharmaceutical storage and retrieval device for the inventory item, moving the inventory item from the port to the identified space by engaging the inventory item with the gripper assembly of the gantry system and moving the gripper assembly with the motor of the gantry system, and linking the inventory item and the identified space and storing the linked information in the database; and wherein when the weight value is not substantially similar to the expected weight, prompting the user to reconcile a difference between the weight value and the expected weight; and wherein when the size of the inventory item is greater than the size of unused space within the pharmaceutical storage and retrieval device, generating an alert to the user.

2. The method of claim 1 wherein determining the size of the inventory item includes:
  acquiring an image of the inventory item in the port:
  calculating the size of the inventory item based on the image of the inventory item.

3. The method of claim 2 wherein identifying the available space includes identifying the available space in the pharmaceutical storage and retrieval device for the inventory item based on the size of the inventory item.

4. The method of claim 1 wherein reading the label on the inventory item to identify the medication type includes reading the label to identify one of an expiration date and a lot number.

5. The method of claim 4 further comprising denying access of the inventory item into the pharmaceutical storage and retrieval device if the inventory item is expired.

6. The method of claim 4 further comprising denying access of the inventory item into the pharmaceutical storage and retrieval device if the inventory item was recalled by a vendor.

7. The method of claim 1 further comprising ordering an additional inventory item from a vendor and comparing the ordered inventory item with the stored medication type, and if the comparison results in a mismatch, generating an alert to the user of the mismatch.

8. The method of claim 1 further comprising determining a weight of packaging of the inventory item by determining a weight of the medication type and subtracting the determined weight of the medication type from the weight value of the inventory item.

9. The method of claim 1 wherein the pharmaceutical storage and retrieval device includes a plurality of shelves positioned within the housing, and wherein identifying the available space includes identifying the available space on the plurality of shelves for the inventory item.

10. The method of claim 1 wherein the gantry system includes a first track, and wherein moving the inventory item from the port to the identified space includes moving the gripper assembly along the first track with the motor.

11. The method of claim 10 wherein the gantry system further includes a second track and a second motor, and wherein moving the inventory item from the port to the identified space also includes moving the first track along the second track with the second motor.

12. The method of claim 1 wherein the pharmaceutical storage and retrieval device includes an interface panel located on the housing, wherein the interface panel includes an access control device, and wherein inputting the identification information includes inputting the identification information into the access control device.

13. The method of claim 12 wherein verifying the identification information includes comparing the identification information of the user to profiles stored in the database.

14. The method of claim 1 wherein the expected weight is a calculated weight value based on a previous weight value of the inventory item and an amount of medication that was expected to be removed from the inventory item prior to positioning the inventory item in the port.

15. The method of claim 1 wherein prompting the user to reconcile the difference between the weight value and the expected weight includes displaying an alert on a monitor coupled to the pharmaceutical storage and retrieval device.

16. The method of claim 1 further comprising closing the door after the inventory item is positioned in the port, and wherein weighing the inventory item includes weighing the inventory item while the inventory item is in the port and the door is closed.

17. A method of stocking a pharmaceutical storage and retrieval device, the pharmaceutical storage and retrieval device including a housing, a port supported by the housing, a first door movably coupled to an exterior of the housing to selectively cover the port, a second door movably coupled to an interior of the housing to selectively cover the port, a scanner supported by the housing within the port, a scale supported by the housing within the port, and a gantry system positioned within the housing, the gantry system including a gripper assembly and a motor coupled to the gripper assembly to move the gripper assembly within the housing, the method comprising:
  inputting identification information of a user into the pharmaceutical storage and retrieval device;
  verifying the identification information of the user of the pharmaceutical storage and retrieval device;
  opening the first door to the port of the device, the port being accessible from outside of the pharmaceutical storage and retrieval device, wherein the port is defined between the first door and the second door of the pharmaceutical storage and retrieval device;
  positioning an inventory item in the port between the first door and the second door and closing the first door;
  weighing the inventory item while the inventory item is in the port and the first door is closed using the scale of the device to determine a weight value of the inventory item;
  storing the weight value of the inventory item in a database;
  reading a label on the inventory item while the inventory item is in the port using the scanner of the device to identify a medication type;
  when the medication type is not included in the National Drug Code database;
    generating an alert on a user interface of the pharmaceutical storage and retrieval device,
    opening the first door to the port of the device, and
    removing the inventory item from the port;
  storing the medication type in the database;
  determining, by a processor coupled to the database, an amount of medication within the inventory item based on the weight value from the scale and the medication type from the scanner;
  storing a value indicative of the amount of medication within the inventory item in the database;
  identifying an available space in the pharmaceutical storage and retrieval device for the inventory item;
  moving the inventory item from the port to the identified space by engaging the inventory item with the gripper assembly of the gantry system and moving the gripper assembly with the motor of the gantry system; and
  linking the inventory item and the identified space and storing the linked information in the database;
  determining a size of unused space in the pharmaceutical storage and retrieval device; and
  determining a size of the inventory item, wherein when the size of the inventory item is greater than the size of unused space within the pharmaceutical storage and retrieval device, generating an alert to the user.

* * * * *